(12) United States Patent
Epple et al.

(10) Patent No.: US 7,745,445 B2
(45) Date of Patent: Jun. 29, 2010

(54) COMPOUNDS AND COMPOSITIONS AS PPAR MODULATORS

(75) Inventors: Robert Epple, San Diego, CA (US); Mihai Azimioara, La Jolla, CA (US)

(73) Assignee: IRM LLC, Hamilton (BM)

( * ) Notice: Subject to any disclaimer, the term of this patent is extended or adjusted under 35 U.S.C. 154(b) by 703 days.

(21) Appl. No.: 11/596,598

(22) PCT Filed: May 13, 2005

(86) PCT No.: PCT/US2005/016747

§ 371 (c)(1), (2), (4) Date: Nov. 14, 2006

(87) PCT Pub. No.: WO2005/113506

PCT Pub. Date: Dec. 1, 2005

(65) Prior Publication Data

US 2007/0259890 A1    Nov. 8, 2007

Related U.S. Application Data

(60) Provisional application No. 60/571,004, filed on May 14, 2004.

(51) Int. Cl.
*A61K 31/47* (2006.01)
*C07D 215/00* (2006.01)

(52) U.S. Cl. .................. 514/256; 514/311; 514/332; 514/438; 514/464; 514/443; 514/461; 514/468; 514/469; 514/557; 544/335; 546/174; 546/342; 549/29; 549/31; 549/32; 549/429; 549/433; 549/434; 560/55

(58) Field of Classification Search .................. None
See application file for complete search history.

(56) References Cited

U.S. PATENT DOCUMENTS 6,555,577 B1    4/2003    Morgensen

FOREIGN PATENT DOCUMENTS

| JP | 08333287 A | * | 12/1996 |
| WO | WO 92/01675 | * | 2/1992 |
| WO | WO 02/076438 A2 | * | 10/2002 |
| WO | WO03084916 A3 | | 10/2003 |

* cited by examiner

*Primary Examiner*—Zinna N Davis
(74) *Attorney, Agent, or Firm*—Scott W. Reid; Genomics Institute of the Novartis Research Foundation

(57) ABSTRACT

The invention provides compounds, pharmaceutical compositions comprising such compounds and methods of using such compounds to treat or prevent diseases or disorders associated with the activity of the Peroxisome Proliferator-Activated Receptor (PPAR) families, particularly the activity of PPARδ.

5 Claims, No Drawings

COMPOUNDS AND COMPOSITIONS AS PPAR MODULATORS

CROSS-REFERENCE TO RELATED APPLICATIONS

This application is a 371 U.S. national phase application of international application number PCT/US2005/016747 filed 13 May 2005, which application claims priority to U.S. Provisional Patent Application No. 60/571,004, filed 14 May 2004. The full disclosure of this application is incorporated herein by reference in its entirety and for all purposes.

BACKGROUND OF THE INVENTION

1. Field of the Invention

The invention provides compounds, pharmaceutical compositions comprising such compounds and methods of using such compounds to treat or prevent diseases or disorders associated with the activity of the Peroxisome Proliferator-Activated Receptor (PPAR) families, particularly the activity of PPARδ.

2. Background

Peroxisome Proliferator Activated Receptors (PPARs) are members of the nuclear hormone receptor super family, which are ligand-activated transcription factors regulating gene expression. Certain PPARs are associated with a number of disease states including dyslipidemia, hyperlipidemia, hypercholesteremia, atherosclerosis, atherogenesis, hypertriglyceridemia, heart failure, myocardial infarction, vascular diseases, cardiovascular diseases, hypertension, obesity, inflammation, arthritis, cancer, Alzheimer's disease, skin disorders, respiratory diseases, ophthalmic disorders, IBDs (irritable bowel disease), ulcerative colitis and Crohn's disease. Accordingly, molecules that modulate the activity of PPARs, particularly PPARδ, are useful as therapeutic agents in the treatment of such diseases.

SUMMARY OF THE INVENTION

In one aspect, the present invention provides compounds of Formula I:

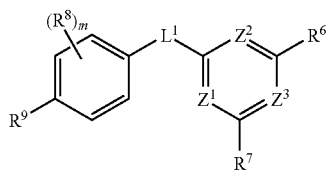

in which:

m is an integer selected from 1, 2 and 3;

$Z^1$, $Z^2$ and $Z^3$ are members independently selected from CH and N;

$L^1$ is selected from —XOX— and —XS(O)$_{0-2}$X—; wherein X is independently selected from a bond and $C_{1-4}$alkylene; wherein any alkylene of $L^1$ can be optionally substituted by 1 to 3 radicals selected from halo, $C_{1-6}$alkyl, $C_{1-6}$alkoxy, halo-substituted-$C_{1-6}$alkyl and halo-substituted-$C_{1-6}$alkoxy;

$R^6$ and $R^7$ are independently selected from —$R^{10}$ and —$YR^{10}$; wherein Y is a selected from $C_{1-6}$alkylene, $C_{2-6}$alkenylene and $C_{2-6}$alkynylene; and $R^{10}$ is selected from $C_{3-12}$cycloalkyl, $C_{3-8}$heterocycloalkyl, $C_{6-10}$aryl and $C_{5-13}$heteroaryl;

wherein any aryl, heteroaryl, cycloalkyl and heterocycloalkyl of $R^{10}$ is optionally substituted with 1 to 3 radicals independently selected from halo, nitro, cyano, $C_{1-6}$alkyl, $C_{1-6}$alkoxy, hydroxy-$C_{1-6}$alkyl, halo-substituted-$C_{1-6}$alkyl, halo-substituted-$C_{1-6}$alkoxy, —XS(O)$_{0-2}$X$R^{11}$, —XS(O)$_{0-2}$X$R^{12}$, —XNR$^{11}$R$^{11}$, —XNR$^{11}$X$R^{12}$ and —XOXR$^{12}$; wherein X is a bond or $C_{1-4}$alkylene; $R^{11}$ is selected from hydrogen and $C_{1-6}$alkyl; and $R^{12}$ is selected from $C_{3-12}$cycloalkyl, $C_{3-8}$heterocycloalkyl, $C_{6-10}$aryl and $C_{5-10}$heteroaryl; wherein any aryl, heteroaryl, cycloalkyl and heterocycloalkyl of $R^{12}$ is optionally substituted with 1 to 3 radicals independently selected from halo, nitro, cyano, $C_{1-6}$alkyl, $C_{1-6}$alkoxy, halo-substituted-$C_{1-6}$alkyl and halo-substituted-$C_{1-6}$alkoxy;

$R^8$ is selected from halo, $C_{1-6}$alkyl, $C_{1-6}$alkoxy, hydroxy-$C_{1-6}$alkyl, halo-substituted-$C_{1-6}$alkyl, halo-substituted-$C_{1-6}$alkoxy, $C_{6-10}$aryl, $C_{5-10}$heteraryl, $C_{3-12}$cycloalkyl and $C_{3-8}$heterocycloalkyl; wherein any aryl, heteroaryl, cycloalkyl and heterocycloalkyl of $R^8$ is optionally substituted with 1 to 3 radicals independently selected from halo, nitro, cyano, $C_{1-6}$alkyl, $C_{1-6}$alkoxy, hydroxy-$C_{1-6}$alkyl, halo-substituted-$C_{1-6}$alkyl and halo-substituted-$C_{1-6}$alkoxy;

$R^9$ is selected from —XOXC(O)OR$^{11}$ and —XC(O)OR$^{11}$; wherein X is a bond or $C_{1-4}$alkylene; and $R^{11}$ is selected from hydrogen and $C_{1-6}$alkyl; and the N-oxide derivatives, prodrug derivatives, protected derivatives, individual isomers and mixture of isomers thereof; and the pharmaceutically acceptable salts and solvates (e.g. hydrates) of such compounds.

In a second aspect, the present invention provides a pharmaceutical composition which contains a compound of Formula I or a N-oxide derivative, individual isomers and mixture of isomers thereof; or a pharmaceutically acceptable salt thereof, in admixture with one or more suitable excipients.

In a third aspect, the present invention provides a method of treating a disease in an animal in which modulation of PPAR activity, particularly PPARδ, can prevent, inhibit or ameliorate the pathology and/or symptomology of the diseases, which method comprises administering to the animal a therapeutically effective amount of a compound of Formula I or a N-oxide derivative, individual isomers and mixture of isomers thereof, or a pharmaceutically acceptable salt thereof.

In a fourth aspect, the present invention provides the use of a compound of Formula I in the manufacture of a medicament for treating a disease in an animal in which PPAR activity, particularly PPARδ, activity contributes to the pathology and/ or symptomology of the disease.

In a fifth aspect, the present invention provides a process for preparing compounds of Formula I and the N-oxide derivatives, prodrug derivatives, protected derivatives, individual isomers and mixture of isomers thereof, and the pharmaceutically acceptable salts thereof.

DETAILED DESCRIPTION OF THE INVENTION

Definitions

"Alkyl" as a group and as a structural element of other groups, for example halo-substituted-alkyl and alkoxy, can be either straight-chained or branched. $C_{1-6}$alkoxy includes, methoxy, ethoxy, and the like. Halo-substituted alkyl includes trifluoromethyl, pentafluoroethyl, and the like.

"Aryl" means a monocyclic or fused bicyclic aromatic ring assembly containing six to ten ring carbon atoms. For example, aryl can be phenyl or naphthyl, preferably phenyl. "Arylene" means a divalent radical derived from an aryl group.

"Heteroaryl" is as defined for aryl where one or more of the ring members are a heteroatom. For example heteroaryl includes pyridyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, tetrazolyl, pyrazolyl, thienyl, etc. "$C_{6-10}arylC_{0-4}alkyl$" means an aryl as described above connected via a alkylene grouping. For example, $C_{6-10}arylC_{0-4}alkyl$ includes phenethyl, benzyl, etc.

"Cycloalkyl" means a saturated or partially unsaturated, monocyclic, fused bicyclic or bridged polycyclic ring assembly containing the number of ring atoms indicated. For example, $C_{3-10}cycloalkyl$ includes cyclopropyl, cyclobutyl, cyclopentyl, cyclohexyl, etc.

"Heterocycloalkyl" means cycloalkyl, as defined in this application, provided that one or more of the ring carbons indicated, are replaced by a moiety selected from —O—, —N=, —NR—, —C(O)—, —S—, —S(O)— or —S(O)$_2$—, wherein R is hydrogen, $C_{1-4}alkyl$ or a nitrogen protecting group. For example, $C_{3-8}heterocycloalkyl$ as used in this application to describe compounds of the invention includes morpholino, pyrrolidinyl, piperazinyl, piperidinyl, piperidinylone, 1,4-dioxa-8-aza-spiro[4,5]dec-8-yl, etc.

"Halogen" (or halo) preferably represents chloro or fluoro, but can also be bromo or iodo.

"Treat", "treating" and "treatment" refer to a method of alleviating or abating a disease and/or its attendant symptoms.

DESCRIPTION OF THE PREFERRED EMBODIMENTS

The present invention provides compounds, compositions and methods for the treatment of diseases in which modulation of PPARδ activity can prevent, inhibit or ameliorate the pathology and/or symptomology of the diseases, which method comprises administering to the animal a therapeutically effective amount of a compound of Formula I.

In one embodiment, with reference to compounds of Formula I, m is an integer selected from 1 to 3; $Z^1$, $Z^2$ and $Z^3$ are members independently selected from CH and N; $L^1$ is selected from —XOX— and —XSX—; wherein X is independently selected from a bond and $C_{1-4}alkylene$; $R^6$ and $R^7$ are independently selected from —$R^{10}$ and —$YR^{10}$; wherein Y is a selected from $C_{1-6}alkylene$ and $C_{2-6}alkenylene$; and $R^{10}$ is selected from $C_{6-10}aryl$ and $C_{5-13}heteroaryl$; wherein any aryl or heteroaryl of $R^{10}$ is optionally substituted with 1 to 3 radicals independently selected from halo, cyano, $C_{1-6}alkyl$, $C_{1-6}alkoxy$, hydroxy-$C_{1-6}alkyl$, halo-substituted-$C_{1-6}alkyl$, halo-substituted-$C_{1-6}alkoxy$, —XS(O)$_{0-2}XR^{11}$, —XNR$^{11}$R$^{11}$ and —XOXR$^{12}$; wherein X is a bond or $C_{1-4}alkylene$; $R^{11}$ is selected from hydrogen and $C_{1-6}alkyl$; and $R^{12}$ is $C_{6-10}aryl$; $R^8$ is $C_{1-6}alkyl$; and $R^9$ is —XOXC(O)OR$^{11}$; wherein X is a bond or $C_{1-4}alkylene$; and $R^{11}$ is selected from hydrogen and $C_{1-6}alkyl$.

In another embodiment, the invention provides a compound of Formula Ia:

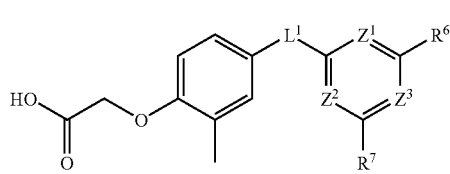

Ia in which:

$Z^1$, $Z^2$ and $Z^3$ are members independently selected from CH and N;

$L^1$ is selected from —CH$_2$O—, —OCH$_2$— and —SCH$_2$—;

$R^6$ and $R^7$ are independently selected from —$R^{10}$ and —$YR^{10}$; wherein Y is propenylene; and $R^{10}$ is selected from phenyl, biphenyl, naphthyl, benzo[b]furanyl, pyridinyl, pyrimidinyl, dibenzo-furan-2-yl, furanyl, benzo[b]thiophene, thienyl and quinolinyl; wherein any aryl or heteroaryl of $R^{10}$ is optionally substituted with 1 to 3 radicals independently selected from halo, cyano, methyl, hydroxy-methyl, methyl-sulfanyl, methoxy, trifluoromethyl, trifluoromethoxy, phenoxy, ethyl-sulfonyl and dimethylamino.

In another embodiment, are compounds of Formula Ib:

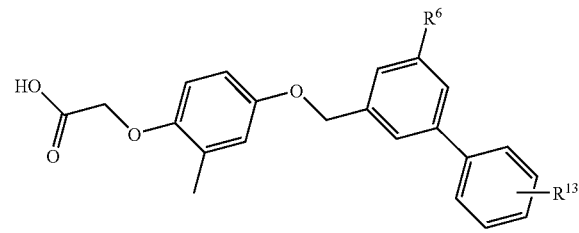

Ib in which $R^6$ is selected from —$R^{10}$ and —$YR^{10}$; wherein Y is propenylene; and $R^{10}$ is selected from phenyl, biphenyl, naphthyl, benzo[b]furanyl, pyridinyl, pyrimidinyl, dibenzo-furan-2-yl, furanyl, benzo[b]thiophene, thienyl and quinolinyl; wherein any aryl or heteroaryl of $R^{10}$ is optionally substituted with 1 to 3 radicals independently selected from halo, cyano, methyl, hydroxy-methyl, methyl-sulfanyl, methoxy, trifluoromethyl, trifluoromethoxy, phenoxy, ethyl-sulfonyl and dimethylamino; and $R^{13}$ is selected from methoxy, trifluoromethyl and trifluoromethoxy.

Preferred compounds of Formula I are detailed in the Examples, infra.

Pharmacology and Utility

Compounds of the invention modulate the activity of PPARs and, as such, are useful for treating diseases or disorders in which PPARs contributes to the pathology and/or symptomology of the disease. This invention further provides compounds of this invention for use in the preparation of medicaments for the treatment of diseases or disorders in which PPARs, particularly PPARδ, contributes to the pathology and/or symptomology of the disease.

Such compounds may therefore be employed for the treatment of prophylaxis, dyslipidemia, hyperlipidemia, hypercholesteremia, atherosclerosis, atherogenesis, hypertriglyceridemia, heart failure, hyper cholesteremia, myocardial infarction, vascular diseases, cardiovascular diseases, hypertension, obesity, cachexia, HIV wasting syndrome, inflammation, arthritis, cancer, Alzheimer's disease, anorexia, anorexia nervosa, bulimia, skin disorders, respiratory diseases, ophthalmic disorders, IBDs (irritable bowel disease), ulcerative colitis and Crohn's disease. Preferably for the treatment of prophylaxis, dyslipidemia, hyperlipidemia, hypercholesteremia, atherosclerosis, atherogenesis, hypertriglyceridemia, cardiovascular diseases, hypertension, obesity, inflammation, cancer, skin disorders, IBDs (irritable bowel disease), ulcerative colitis and Crohn's disease.

Compounds of the invention can also be employed to treat long term critical illness, increase muscle mass and/or muscle strength, increase lean body mass, maintain muscle strength and function in the elderly, enhance muscle endurance and muscle function, and reverse or prevent frailty in the elderly.

Further, the compounds of the present invention may be employed in mammals as hypoglycemic agents for the treatment and prevention of conditions in which impaired glucose tolerance, hyperglycemia and insulin resistance are implicated, such as type-1 and type-2 diabetes, Impaired Glucose Metabolism (IGM), Impaired Glucose Tolerance (IGT), Impaired Fasting Glucose (IFG), and Syndrome X. Preferably type-1 and type-2 diabetes, Impaired Glucose Metabolism (IGM), Impaired Glucose Tolerance (IGT) and Impaired Fasting Glucose (IFG).

In accordance with the foregoing, the present invention further provides a method for preventing or treating any of the diseases or disorders described above in a subject in need of such treatment, which method comprises administering to said subject a therapeutically effective amount (See, "Administration and Pharmaceutical Compositions", infra) of a compound of the invention or a pharmaceutically acceptable salt thereof. For any of the above uses, the required dosage will vary depending on the mode of administration, the particular condition to be treated and the effect desired. The present invention also concerns: i) a compound of the invention or a pharmaceutically acceptable salt thereof for use as a medicament; and ii) the use of a compound of the invention or a pharmaceutically acceptable salt thereof for the manufacture of a medicament for preventing or treating any of the diseases or disorders described above.

Administration and Pharmaceutical Compositions

In general, compounds of the invention will be administered in therapeutically effective amounts via any of the usual and acceptable modes known in the art, either singly or in combination with one or more therapeutic agents. A therapeutically effective amount can vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrollidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions can be sterilized and/or contain adjuvants, such as preserving, stabilizing, wetting or emulsifying agents, solution promoters, salts for regulating the osmotic pressure and/or buffers. In addition, they can also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations can also be used. Suitable formulations for topical application, e.g., to the skin and eyes, are preferably aqueous solutions, ointments, creams or gels well-known in the art. Such can contain solubilizers, stabilizers, tonicity enhancing agents, buffers and preservatives.

This invention also concerns a pharmaceutical composition comprising a therapeutically effective amount of a compound as described herein in combination with one or more pharmaceutically acceptable carriers.

Compounds of the invention can be administered in therapeutically effective amounts in combination with one or more therapeutic agents (pharmaceutical combinations).

Thus, the present invention also relates to pharmaceutical combinations, such as a combined preparation or pharmaceutical composition (fixed combination), comprising: 1) a compound of the invention as defined above or a pharmaceutical acceptable salt thereof; and 2) at least one active ingredient selected from:

a) anti-diabetic agents such as insulin, insulin derivatives and mimetics; insulin secretagogues such as the sulfonylureas, e.g., Glipizide, glyburide and Amaryl; insulinotropic sulfonylurea receptor ligands such as meglitinides, e.g., nateglinide and repaglinide; insulin sensitizer such as protein tyrosine phosphatase-1B (PTP-1B) inhibitors such as PTP-112; GSK3 (glycogen synthase kinase-3) inhibitors such as SB-517955, SB-4195052, SB-216763, N,N-57-05441 and N,N-57-05445; RXR ligands such as GW-0791 and AGN-194204; sodium-dependent glucose co-transporter inhibitors such as T-1095; glycogen phosphorylase A inhibitors such as BAY R3401; biguanides such as metformin; alpha-glucosidase inhibitors such as acarbose; GLP-1 (glucagon like peptide-1), GLP-1 analogs such as Exendin-4 and GLP-1 mimetics; DPPIV (dipeptidyl peptidase IV) inhibitors such as DPP728, LAF237 (vildagliptin—Example 1 of WO 00/34241), MK-0431, saxagliptin, GSK23A; an AGE breaker; a thiazolidone derivative (glitazone) such as pioglitazone, rosiglitazone, or (R)-1-{4-[5-methyl-2-(4-trifluoromethyl-phenyl)-oxazol-4-ylmethoxy]-benzenesulfonyl}-2,3-dihydro-1H-indole-2-carboxylic acid described in the patent application WO 03/043985, as compound 19 of Example 4, a non-glitazone type PPARγ agonist e.g. GI-262570;

b) hypolipidemic agents such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin and rivastatin; squalene synthase inhibitors; FXR (farnesoid X receptor) and LXR (liver X receptor) ligands; cholestyramine; fibrates; nicotinic acid and aspirin;

c) an anti-obesity agent or appetite regulating agent such as phentermine, leptin, bromocriptine, dexamphetamine, amphetamine, fenfluramine, dexfenfluramine, sibutramine, orlistat, dexfenfluramine, mazindol, phentermine, phendimetrazine, diethylpropion, fluoxetine, bupropion, topiramate, diethylpropion, benzphetamine, phenylpropanolamine or ecopipam, ephedrine, pseudoephedrine or cannabinoid receptor antagonists;

d) anti-hypertensive agents, e.g., loop diuretics such as ethacrynic acid, furosemide and torsemide; diuretics such as thiazide derivatives, chlorithiazide, hydrochlorothiazide, amiloride; angiotensin converting enzyme (ACE) inhibitors such as benazepril, captopril, enalapril, fosinopril, lisinopril, moexipril, perinodopril, quinapril, ramipril and trandolapril; inhibitors of the Na-K-ATPase membrane pump such as digoxin; neutralendopeptidase (NEP) inhibitors e.g. thiorphan, terteo-thiorphan, SQ29072; ECE inhibitors e.g. SLV306; ACE/NEP inhibitors such as omapatrilat, sampatrilat and fasidotril; angiotensin II antagonists such as candesartan, eprosartan, irbesartan, losartan, telmisartan and valsartan, in particular valsartan; renin inhibitors such as aliskiren, terlakiren, ditekiren, RO 66-1132, RO-66-1168; β-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; and aldosterone synthase inhibitors;

e) a HDL increasing compound;

f) Cholesterol absorption modulator such as Zetia® and KT6-971;

g) Apo-A1 analogues and mimetics;

h) thrombin inhibitors such as Ximelagatran;

i) aldosterone inhibitors such as anastrazole, fadrazole, eplerenone;

j) Inhibitors of platelet aggregation such as aspirin, clopidogrel bisulfate;

k) estrogen, testosterone, a selective estrogen receptor modulator, a selective androgen receptor modulator;

l) a chemotherapeutic agent such as aromatase inhibitors e.g. femara, anti-estrogens, topoisomerase I inhibitors, topoisomerase II inhibitors, microtubule active agents, alkylating agents, antineoplastic antimetabolites, platin compounds, compounds decreasing the protein kinase activity such as a PDGF receptor tyrosine kinase inhibitor preferably Imatinib ({N-{5-[4-(4-methyl-piperazino-methyl)-benzoylamido]-2-methylphenyl}-4-(3-pyridyl)-2-pyrimidine-amine}) described in the European patent application EP-A-0 564 409 as example 21 or 4-Methyl-N-[3-(4-methyl-imidazol-1-yl)-5-trifluoromethyl-phenyl]-3-(4-pyridin-3-yl-pyrimidin-2-ylamino)-benzamide described in the patent application WO 04/005281 as example 92; and m) an agent interacting with a 5-HT₃ receptor and/or an agent interacting with 5-HT₄ receptor such as tegaserod described in the U.S. Pat. No. 5,510,353 as example 13, tegaserod hydrogen maleate, cisapride, cilansetron;

or, in each case a pharmaceutically acceptable salt thereof; and optionally a pharmaceutically acceptable carrier.

Most preferred combination partners are tegaserod, imatinib, vildagliptin, metformin, a thiazolidone derivative (glitazone) such as pioglitazone, rosiglitazone, or (R)-1-{4-[5-methyl-2-(4-trifluoromethyl-phenyl)-oxazol-4-ylmethoxy]-benzenesulfonyl}-2,3-dihydro-1H-indole-2-carboxylic acid, a sulfonylurea receptor ligand, aliskiren, valsartan, orlistat or a statin such as pitavastatin, simvastatin, fluvastatin or pravastatin.

Preferably the pharmaceutical combinations contains a therapeutically effective amount of a compound of the invention as defined above, in a combination with a therapeutically effective amount of another therapeutic agent as described above, e.g., each at an effective therapeutic dose as reported in the art. Combination partners (1) and (2) can be administered together, one after the other or separately in one combined unit dosage form or in two separate unit dosage forms. The unit dosage form may also be a fixed combination.

The structure of the active agents identified by generic or trade names may be taken from the actual edition of the standard compendium "The Merck Index" or the Physician's Desk Reference or from databases, e.g. Patents International (e.g. IMS World Publications) or Current Drugs. The corresponding content thereof is hereby incorporated by reference. Any person skilled in the art is fully enabled to identify the active agents and, based on these references, likewise enabled to manufacture and test the pharmaceutical indications and properties in standard test models, both in vitro and in vivo.

In another preferred aspect the invention concerns a pharmaceutical composition (fixed combination) comprising a therapeutically effective amount of a compound as described herein, in combination with a therapeutically effective amount of at least one active ingredient selected from the above described group a) to m), or, in each case a pharmaceutically acceptable salt thereof.

A pharmaceutical composition or combination as described herein for the manufacture of a medicament for the treatment of for the treatment of dyslipidemia, hyperlipidemia, hypercholesteremia, atherosclerosis, hypertriglyceridemia, heart failure, myocardial infarction, vascular diseases, cardiovascular diseases, hypertension, obesity, inflammation, arthritis, cancer, Alzheimer's disease, skin disorders, respiratory diseases, ophthalmic disorders, inflammatory bowel diseases, IBDs (irritable bowel disease), ulcerative colitis, Crohn's disease, conditions in which impaired glucose tolerance, hyperglycemia and insulin resistance are implicated, such as type-1 and type-2 diabetes, Impaired Glucose Metabolism (IGM), Impaired Glucose Tolerance (IGT), Impaired Fasting Glucose (IFG), and Syndrome-X.

Such therapeutic agents include estrogen, testosterone, a selective estrogen receptor modulator, a selective androgen receptor modulator, insulin, insulin derivatives and mimetics; insulin secretagogues such as the sulfonylureas, e.g., Glipizide and Amaryl; insulinotropic sulfonylurea receptor ligands, such as meglitinides, e.g., nateglinide and repaglinide; insulin sensitizers, such as protein tyrosine phosphatase-1B (PTP-1B) inhibitors, GSK3 (glycogen synthase kinase-3) inhibitors or RXR ligands; biguanides, such as metformin; alpha-glucosidase inhibitors, such as acarbose; GLP-1 (glucagon like peptide-1), GLP-1 analogs, such as Exendin-4, and GLP-1 mimetics; DPPIV (dipeptidyl peptidase IV) inhibitors, e.g. isoleucin-thiazolidide; DPP728 and LAF237, hypolipidemic agents, such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin, fluindostatin and rivastatin, squalene synthase inhibitors or FXR (liver X receptor) and LXR (farnesoid X receptor) ligands, cholestyramine, fibrates, nicotinic acid and aspirin. A compound of the present invention may be administered either simultaneously, before or after the other active ingredient, either separately by the same or different route of administration or together in the same pharmaceutical formulation.

The invention also provides for pharmaceutical combinations, e.g. a kit, comprising: a) a first agent which is a compound of the invention as disclosed herein, in free form or in pharmaceutically acceptable salt form, and b) at least one co-agent. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula I and a co-agent, are both administered to a patient simultaneously in the form of a single entity or dosage. The term "non-fixed combination" means that the active ingredients, e.g. a compound of Formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

Processes for Making Compounds of the Invention

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

Compounds of Formula I can be prepared by proceeding as in the following Reaction Scheme 1:

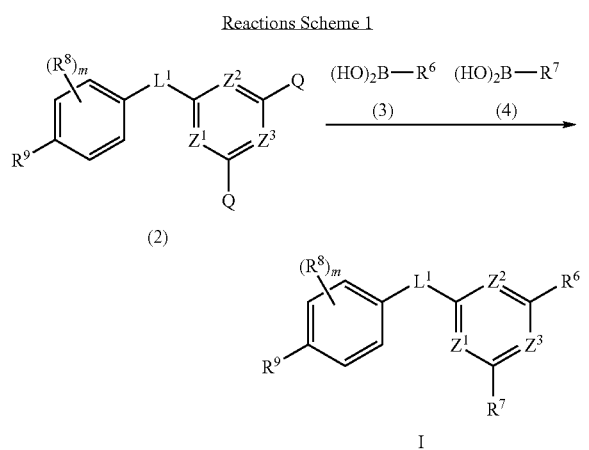

in which m, $L^1$, $R^6$, $R^7$, $R^8$, $R^9$, $Z^1$, $Z^2$ and $Z^3$ are as defined for Formula I in the Summary of the Invention and Q is halo (such as Cl, Br, I and the like). Compounds of Formula I are prepared by reacting a compound of formula 2 with compounds of formula 3 and 4 in the presence of a suitable catalyst (e.g., Pd(PPh$_3$)$_4$, or the like) and suitable solvents (e.g., dioxane, ethanol, and the like). The reaction is carried out (microwaved) in the temperature range of about 150° C. to about 200° C. and takes up to 20 minutes to complete.

An intermediate of Formula I can be prepared by proceeding as in the following Reaction Scheme 2a and 2b:

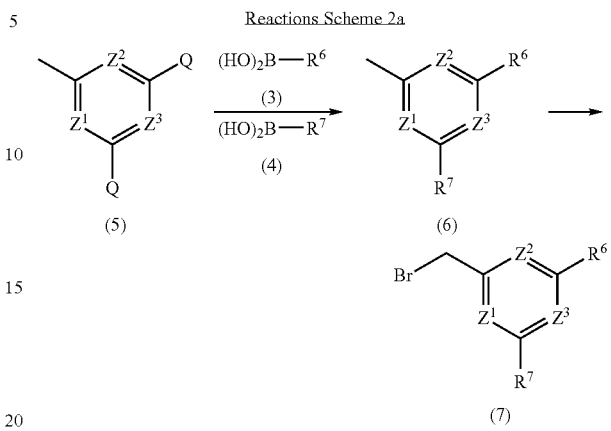

in which $R^6$, $R^7$, $Z^1$, $Z^2$ and $Z^3$ are as defined for Formula I in the Summary of the Invention and Q is halo (such as Cl, Br, I and the like). Compounds of formula 6 are prepared by reacting a compound of formula 5 with compounds of formula 3 and 4 in the presence of a suitable catalyst (e.g., Pd(PPh$_3$)$_4$, or the like) and suitable solvents (e.g., dioxane, ethanol, and the like). The reaction is carried out (microwaved) in the temperature range of about 150° C. to about 200° C. and takes up to 20 minutes to complete. Compounds of formula 6 are further reacted to produce a compound of formula 7 in the presence of a suitable catalyst (e.g., N-Bromosuccinimide (NBS), and the like) and a suitable brominating agent (e.g. azobisisobutyronitrile (AIBN), and the like).

Compounds of Formula I, in which $L^1$ is —OCH$_2$—, can be prepared by proceeding as in the following Reaction Scheme 2b:

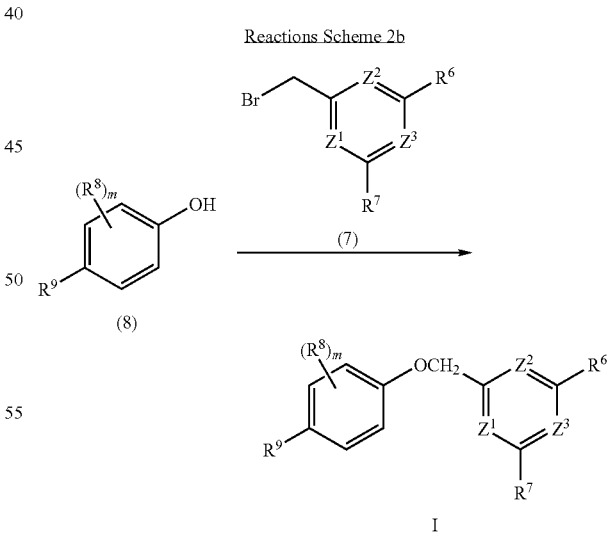

in which m, $R^6$, $R^7$, $R^8$, $R^9$, $Z^1$, $Z^2$ and $Z^3$ are as defined for Formula I in the Summary of the Invention. Compounds of Formula I are prepared by reacting a compound of formula 5 with a compound of formula 6 in the presence of a suitable solvent (e.g., acetonitrile, or the like) and suitable base (e.g., cesium carbonate, and the like). The reaction is carried out under nitrogen and takes up to 30 hours to complete. The reaction can optionally be completed by saponification with, for example, LiOH, and the like.

Additional Processes for Making Compounds of the Invention

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base. Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.)

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", 3$^{rd}$ edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

In summary, the compounds of Formula I can be made by a process, which involves:

(a) that of reaction schemes 1 or 2; and (b) optionally converting a compound of the invention into a pharmaceutically acceptable salt;

(c) optionally converting a salt form of a compound of the invention to a non-salt form;

(d) optionally converting an unoxidized form of a compound of the invention into a pharmaceutically acceptable N-oxide;

(e) optionally converting an N-oxide form of a compound of the invention to its unoxidized form;

(f) optionally resolving an individual isomer of a compound of the invention from a mixture of isomers;

(g) optionally converting a non-derivatized compound of the invention into a pharmaceutically acceptable prodrug derivative; and (h) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

EXAMPLES

The present invention is further exemplified, but not limited, by the following intermediates and examples that illustrate the preparation of compounds of Formula I according to the invention.

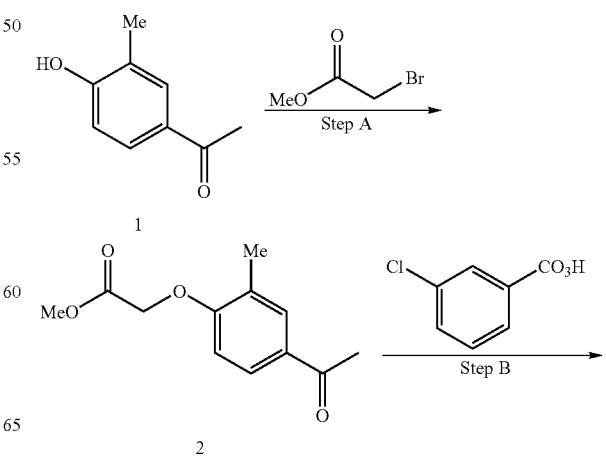

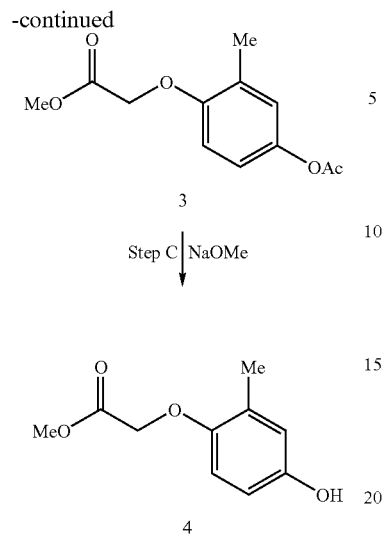
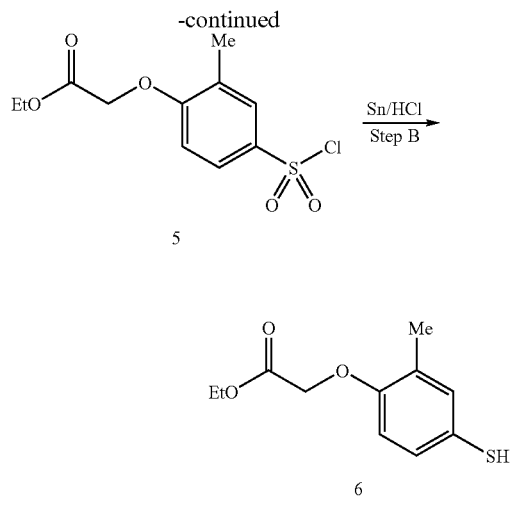

Intermediate 4

(4-Hydroxy-2-methyl-phenoxy)-acetic acid methyl ester

Step A: 4'-Hydroxy-3'-methylacetophenone 1 (25 g, 166.4 mmol) and methyl-bromoacetate (25.5 g, 166.4 mmol) is dissolved in MeCN (600 mL). $Cs_2CO_3$ (117.8 g, 332.9 mmol) is added and the mixture is stirred overnight at room temperature. After insoluble salts are filtered and washed with MeCN, the solvent is removed and the remainder is taken up in EtOAc and washed subsequently with 1 M HCl (3×500 mL) and $H_2O$ (2×500 mL). The organic layer is dried ($MgSO_4$), filtered and concentrated to afford 2 as a white solid.

Step B: (4-Acetyl-2-methyl-phenoxy)-acetic acid methyl ester 2 (33 g, 151.3 mmol), 77% mCPBA (54.9 g, 264.8 mmol) and p-TsOH (2.9 g, 15.1 mmol) in DCM (650 mL) are heated under reflux for 48 hours. The reaction mixture is then washed with 1 M KI (2×500 mL) and $NaHSO_3$ (2×500 mL). The organic layer is dried ($MgSO_4$), filtered and concentrated to afford 3 as a brown syrup.

Step C: A solution of (4-acetoxy-2-methyl-phenoxy)-acetic acid methyl ester 3 (25 g, 105.0 mmol) in dry MeOH (400 mL) is combined with a 0.5 M solution of NaOMe in MeOH (210 mL, 105.0 mmol) and stirred for 1 hour at room temperature. The solution is neutralized with 1 M HCl and washed with $H_2O$ (2×500 mL). The organic layer is dried ($MgSO_4$), filtered and concentrated to afford 4 as a brown solid: $^1$H-NMR (400 MHz, $CD_3OD$) δ=6.65-6.51 (m, 3H), 4.60 (s, 2H), 3.75 (s, 3H), 2.19 (s, 3H). MS calculated for $C_{10}H_{13}O_4$ (M+H$^+$) 197.1. found 197.2.

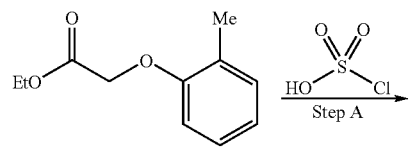

Intermediate 6

(4-Mercapto-2-methyl-phenoxy)-acetic acid ethyl ester

Step A: A 500 mL three-necked round bottom flask is charged with chlorosulfonic acid (25 mL, 373.9 mmol), flushed with nitrogen and cooled to 0° C. Under nitrogen and vigorous stirring, ethyl (2-methylphenoxy)acetate 1 (40 g, 206.2 mmol) is added dropwise. The mixture is stirred for 90 minutes at 0° C., then poured on ice-water (200 mL). After the mixture is stirred for an additional 45 minutes at room temperature, the white precipitate is filtered, washed with ice-water and dried in vacuo to afford 5 as a white solid.

Step B: (4-Chlorosulfonyl-2-methyl-phenoxy)-acetic acid ethyl ester 5 (25 g, 85.4 mmol) and tin (50.8 g, 427 mmol) are suspended in EtOH and cooled to 0° C. After a solution of 4 N HCl in dioxane (107 mL, 427 mmol) is added dropwise, the resulting mixture is heated to reflux for 3 hours. Then the mixture is concentrated in vacuo, the remainder taken up in chloroform and filtered. The filtrate is concentrated in vacuo to a yellow oil, which is purified by chromatography (silica, Hex/EtOAc gradient) to afford 6 as a colorless oil: $^1$H-NMR (400 MHz, $CDCl_3$) δ=7.14 (m, 1H), 7.07-7.10 (m, 1H), 6.59 (m, 1H), 4.60 (s, 2H), 4.25 (q, J=7.1 Hz, 2H), 3.33 (s, 1H), 2.24 (s, 3H), 1.29 (t, J=7.1 Hz, 3H). MS calculated for $C_{11}H_{14}O_3S$ (M+H$^+$) 227.1. found 227.4.

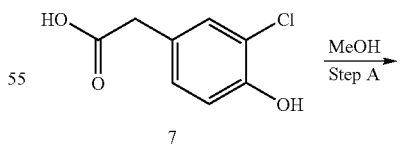

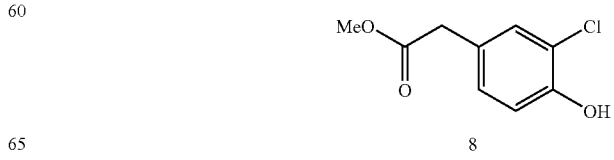

Intermediate 8

(3-Chloro-4-hydroxy-phenyl)-acetic acid methyl ester

Step A: 3-Chloro-4-hydroxy-phenyl)-acetic acid 7 (20 g, 107 mmol) is dissolved in MeOH (250 mL) containing catalytic amounts of conc. $H_2SO_4$ (2.5 mL). The solution is heated to reflux overnight. The solvent is evaporated, the remainder is dissolved in DCM and washed with $H_2O$ (3×200 mL). The organic layer is dried ($MgSO_4$), filtered and concentrated to afford 8 as a light yellow solid: $^1$H-NMR (400 MHz, $CD_3OD$) δ=7.21 (d, J=2.1 Hz, 1H), 7.01 (dd, J=2.1 Hz, J=8.3, 1H), 6.84 (d, J=8.3 Hz, 1H), 3.67 (s, 3H), 3.54 (s, 2H). MS calculated for $C_9H_{10}ClO_3$ (M+H$^+$) 201.0. found 201.2.

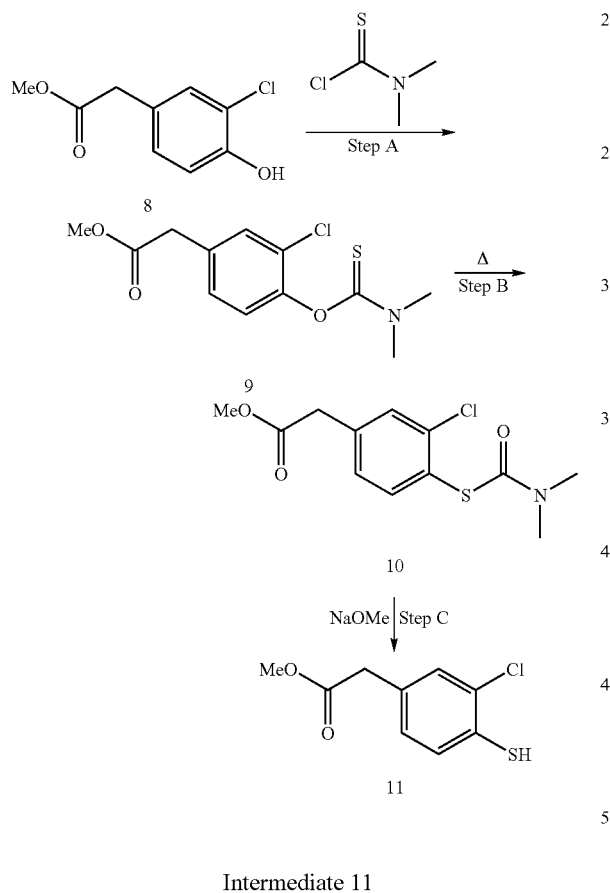

Intermediate 11

(3-Chloro-4-mercapto-phenyl)-acetic acid methyl ester

Step A: 3-(Chloro-4-hydroxy-phenyl)-acetic acid methyl ester 8 (4.1 g, 21.4 mmol), dimethyl thiocarbamoylchloride (3.2 g, 25.6 mmol), $Et_3N$ (5.9 mL, 42.8 mmol) and DMAP (261 mg, 2.14 mmol) are dissolved in dry dioxane (30 mL) and heated to reflux for 16 hours under nitrogen. The reaction mixture is cooled to room temperature, diluted with EtOAc and washed with $H_2O$ (3×50 mL). The organic layer is dried ($MgSO_4$), filtered and concentrated to afford 9 as a colorless oil.

Step B: (3-Chloro-4-dimethylthiocarbamoyloxy-phenyl)-acetic acid methyl ester 9 (5.2 g, 18.1 mmol) is transferred to a 250 mL three-necked round bottom flask equipped with a thermometer. Tetradecane (45 mL) is added and the mixture is heated to reflux (250° C.) overnight. After cooling to room temperature the solvent is decanted, the remaining oil is washed several times with hexanes and purified by chromatography (silica, Hex/EtOAc gradient) to afford 10 as a brown oil.

Step C: (3-Chloro-4-dimethylcarbamoylsulfanyl-phenyl)-acetic acid methyl ester 10 (3.1 g, 10.8 mmol) is dissolved in 0.5 M NaOMe in MeOH. The mixture is heated to reflux for 4 hours, then acidified with 1 M HCl. The organic solvent is evaporated, the remainder is extracted into EtOAc (50 mL) and washed with $H_2O$ (2×50 mL). The organic layer is dried ($MgSO_4$), filtered, concentrated and purified (silica, hexanes/EtOAc gradient) to afford 11 as a pale yellow oil: $^1$H-NMR (400 MHz, $CDCl_3$) δ=7.30-7.26 (m, 2H), 7.06-7.03 (m, 1H) 3.87 (s, 1H), 3.69 (s, 3H), 3.55 (s, 2H). MS calculated for $C_9H_{10}ClO_2S$ (M+H$^+$) 217.0. found 217.3.

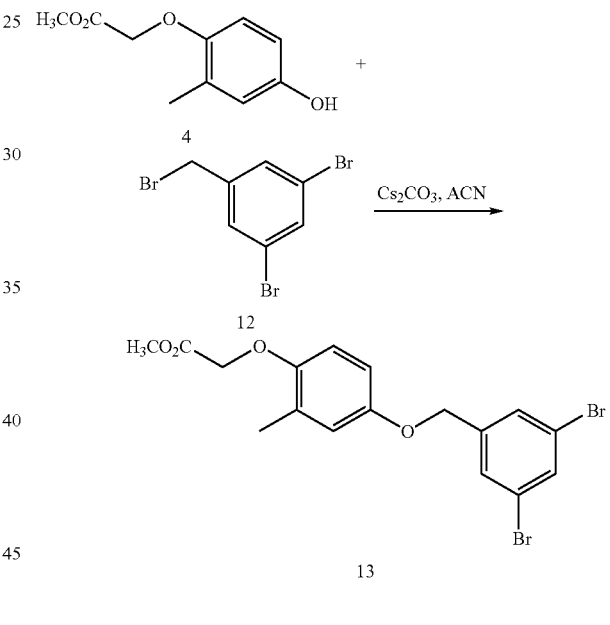

Intermediate 13

[4-(3,5-Dibromo-benzyloxy)-2-methyl-phenoxy]-acetic acid methyl ester

4-Hydroxy-2-methyl-phenoxy)-acetic acid methyl ester 4 (0.36 g, 1.8 mmol) is dissolved in dry acetonitrile (3 mL). Cesium carbonate (1.31 g, 4 mmol) is added, followed by 3,5-dibromobenzyl bromide 12 (0.78 g, 2.37 mmol). The mixture is stirred under nitrogen for 18 hours. The resulting red suspension is filtered, the solids are washed with more acetonitrile, and the resulting clear red solution is concentrated to oil. Silica gel chromatography (10% to 25% ethyl acetate in hexanes) yielded 13 as an oil that slowly solidifies to an off-white crystalline mass. $^1$H-NMR (400 MHz, $CDCl_3$) δ=7.58 (d, J=2 Hz, 1H), 7.47 (d, J=2 Hz, 2H), 6.77 (s, 1H), 6.64 (m, 2H), 4.91 (s, 2H), 4.58 (s, 2H), 3.77 (s, 3H), 2.26 (s, 3H). MS calculated for $C_{17}H_{17}Br_2O_4$ (M+H$^+$) 442.95. found 442.9.

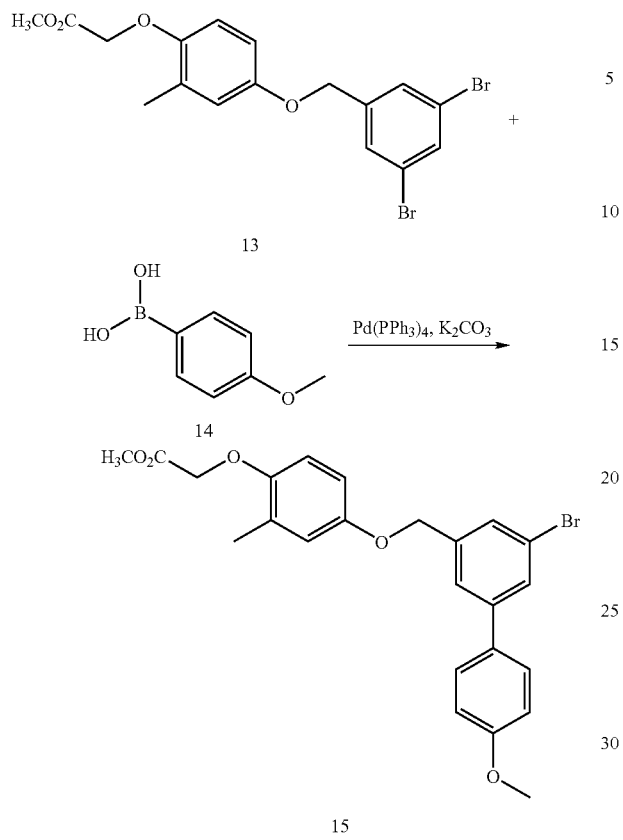

Intermediate 15

[4-(5-Bromo-4'-methoxy-biphenyl-3-ylmethoxy)-2-methyl-phenoxy]-acetic acid methyl ester 4-(3,5-Dibromo-benzyloxy)-2-methyl-phenoxy]-acetic acid methyl ester 13 (1.26 g, 2.8 mmol) is dissolved in dioxane (2 mL). 4-Methoxyphenylboronic acid 14 (0.45 g, 3 mmol) is added, followed by water (0.2 mL), ethanol (0.2 mL), potassium carbonate (0.48 g, 3.5 mmol), and tetrakis (triphenylphosphino)palladium (0.2 g, 0.17 mmol). The mixture is stirred under nitrogen and subjected to microwave (170° C. for 6 minutes). The resulting orange suspension is filtered, the solids are washed with more dioxane, and the resulting solution is purified using reversed-phase HLPC (C18 column, 50% to 100% gradient ACN/water with 0.05% TFA) to yield 15 as an oil. $^1$H-NMR (400 MHz, CDCl$_3$) (rotomers present) δ=7.61-7.46 (m, 5H), 6.96 (m, 2H), 6.9-6.6 (m, 3H), 5.06, 4.98, and 4.90 (3 s, total to 2H), 4.56 (s, 2H), 3.83 (m, 3H), 3.77 (s, 3H), 2.25 (s, 3H). MS calculated for C$_{24}$H$_{24}$BrO$_5$ (M+H$^+$) 471.08. found 471.3.

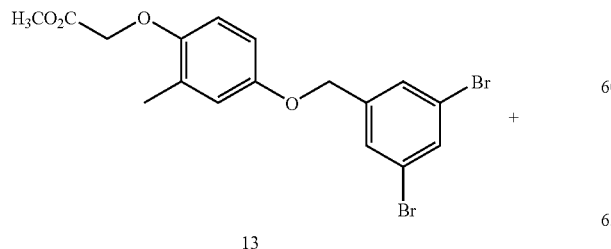

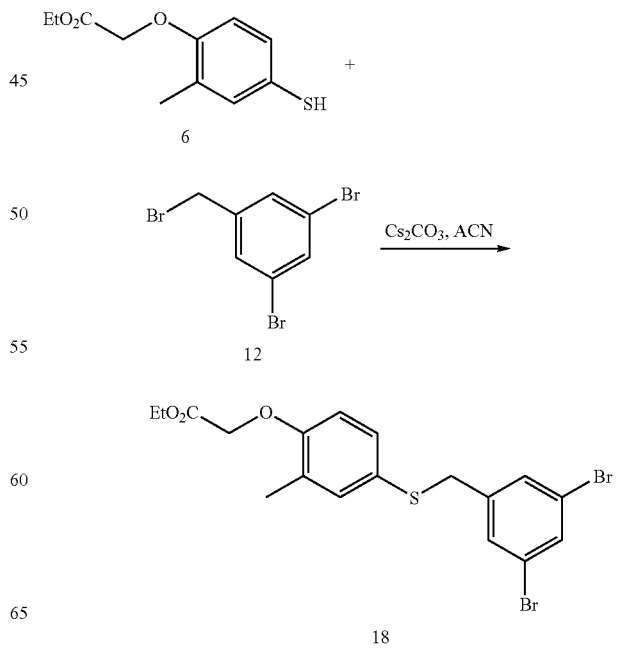

Intermediate 17

[4-(5-Bromo-4'-trifluoromethyl-biphenyl-3-yl-methoxy)-2-methyl-phenoxy]-acetic acid methyl ester A similar synthetic procedure used for 15 is used to prepare 17 as a solid. $^1$H-NMR (400 MHz, CDCl$_3$) δ=7.71-7.65 (m, 5H), 7.61 (s, 1H), 7.56 (s, 1H), 6.84 (d, J=2.8 Hz, 1H), 6.72 (dd, J=8.8, 2.8 Hz, 1H), 6.67 (d, J=8.8 Hz, 1H) 5.03 (s, 2H), 4.61 (s, 2H), 3.80 (s, 3H), 2.29 (s, 3H). MS calculated for C$_{23}$H$_{19}$BrF$_3$O$_4$ (M+H$^+$) 509.06. found 509.0.

Intermediate 18

[4-(3,5-Dibromo-benzylsulfanyl)-2-methyl-phenoxy]-acetic acid ethyl ester

4-Mercapto-2-methyl-phenoxy)-acetic acid ethyl ester 6 (0.23 g, 1.02 mmol) is dissolved in dry acetonitrile (3 mL). Cesium carbonate (0.47 g, 1.44 mmol) is added, followed by 3,5-dibromobenzyl bromide 12 (0.38 g, 1.16 mmol). The mixture is stirred at room temperature under nitrogen for 18 hours. The resulting red suspension is poured over 1N aqueous HCl (20 mL). Extraction with dichloromethane, drying over MgSO$_4$ and concentration in vacuo yielded oil. Silica gel chromatography (5% to 25% ethyl acetate in hexanes) yielded 18 as an oil. $^1$H-NMR (400 MHz, CDCl$_3$) δ=7.51 (s, 1H), 7.23 (s, 2H), 7.12 (d, J=2 Hz, 1H), 7.06 (dd, J=8.4, 2.0 Hz, 1H), 6.60 (d, J=8.4 Hz, 1H), 4.62 (s, 2H), 4.26 (q, J=6.8 Hz, 2H), 3.85 (s, 2H), 2.25 (s, 3H), 1.29 (t, J=6.8 Hz, 3H). MS calculated for C$_{18}$H$_{18}$Br$_2$O$_3$S (M+H$^+$) 472.9. found 472.9.

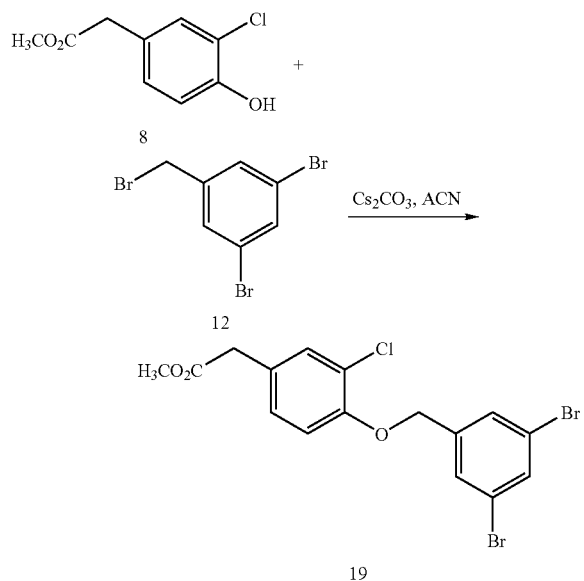

Intermediate 19

[3-Chloro-4-(3,5-dibromo-benzyloxy)-phenyl]-acetic acid methyl ester

A similar procedure used to synthesize intermediate 18 is used for 19. $^1$H-NMR (400 MHz, CDCl$_3$) δ=7.63 (s, 1H), 7.55 (s, 2H), 7.34 (d, J=2 Hz, 1H), 7.11 (dd, J=8.4, 2.0 Hz, 1H), 6.86 (d, J=8.4 Hz, 1H), 5.06 (s, 2H), 3.70 (s, 3H), 3.55 (s, 2H). MS calculated for C$_{16}$H$_{14}$Br$_2$ClO$_3$ (M+H$^+$) 446.9, found 446.9.

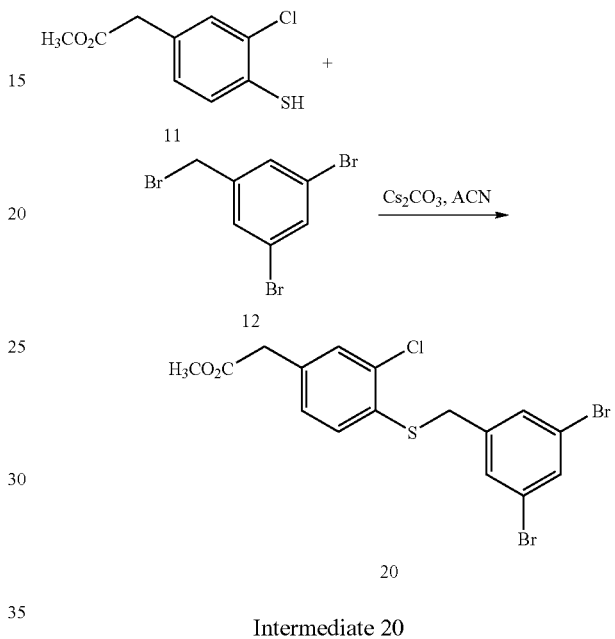

Intermediate 20

[3-Chloro-4-(3,5-dibromo-benzylsulfanyl)-phenyl]-acetic acid methyl ester

A similar procedure used to synthesize intermediate 18 is used for 20. $^1$H-NMR (400 MHz, CDCl$_3$) δ=7.54 (s, 1H), 7.35 (m, 3H), 7.16 (d, J=8.0 Hz, 1H), 7.09 (dd, J=8.0, 1.2 Hz, 1H), 4.02 (s, 2H), 3.70 (s, 3H), 3.57 (s, 2H). MS calculated for C$_{16}$H$_{14}$Br$_2$ClO$_3$ (M+H$^+$) 462.9. found 462.8.

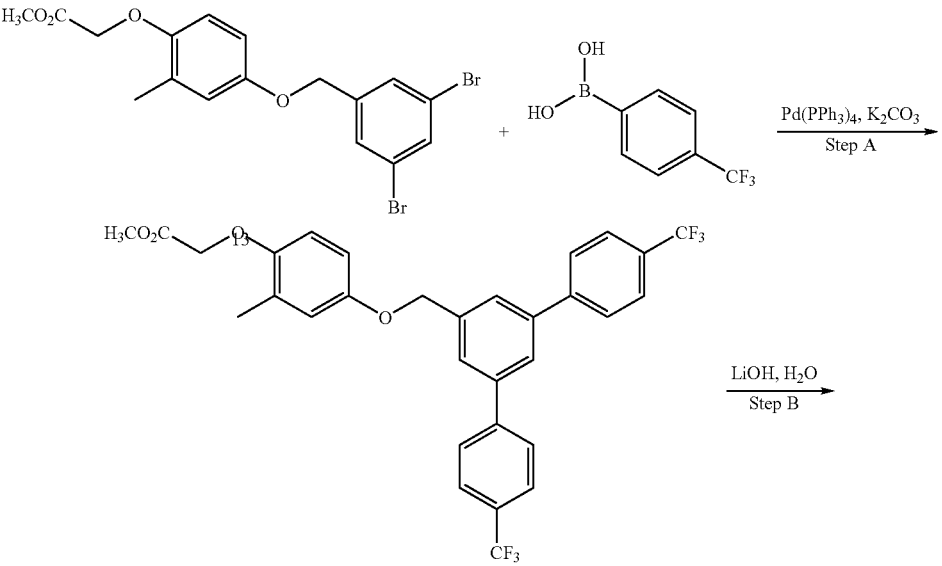

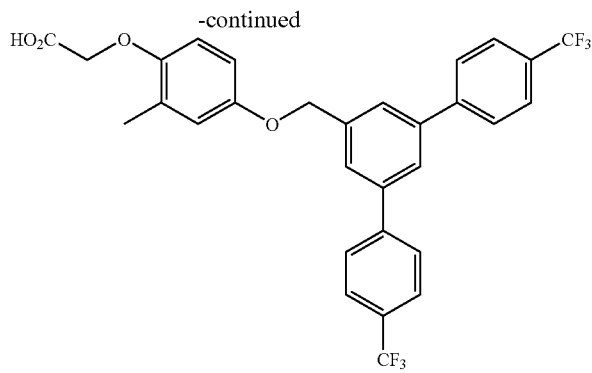

A1

Example A1

[4-(3,5-Bis(4-trifluoromethylphenyl)-benzyloxy)-2-methyl-phenoxy]-acetic acid

Step A: [4-(3,5-Dibromo-benzyloxy)-2-methyl-phenoxy]-acetic acid methyl ester 13 (0.0375 g, 0.088 mmol) is dissolved in dioxane (1 mL). 4-Trifluoromethyl-phenylboronic acid (0.0514 g, 0.27 mmol) is added, followed by water (0.01 mL), ethanol (0.01 mL), potassium carbonate (0.0557 g, 0.4 mmol), and tetrakis-(triphenylphosphino)palladium (0.117 g, 0.01 mmol). The mixture is stirred under nitrogen and subjected to microwave (170° C. for 10 min). The resulting orange suspension is filtered, the solids are washed with more dioxane, and the resulting solution is concentrated and purified by silica gel chromatography (10% to 25% ethyl acetate in hexanes) to yield [4-(3,5-bis(4-trifluoromethylphenyl)-benzyloxy)-2-methyl-phenoxy]-acetic acid methyl ester as an oil. $^1$H-NMR (400 MHz, CDCl$_3$) δ=7.77-7.64 (m, 8H), 7.52 (s, 2H), 7.34 (s, 1H), 6.88 (d, J=2.8 Hz, 1H), 6.76 (dd, J=9.0, 2.8 Hz, 1H), 6.68 (d, J=9.2 Hz, 1H), 5.14 (s, 2H), 4.61 (s, 2H), 3.80 (s, 3H), 2.95 (s, 3H). $^{19}$F-NMR (376 MHz, CDCl$_3$) δ=−62.4.

Step B: The crude [4-(3,5-bis(4-trifluoromethylphenyl)-benzyloxy)-2-methyl-phenoxy]-acetic acid methyl ester from Step A above is dissolved in dioxane (2 mL). Solid lithium hydroxide monohydrate (18 mg, 0.44 mmol, excess) is added, followed by water (0.2 mL). After 1 hour, the mixture is concentrated to dryness. Purification by reversed-phase HPLC yields [4-(3,5-bis(4-trifluoromethylphenyl)-benzyloxy)-2-methyl-phenoxy]-acetic acid A1 as a solid. $^1$H-NMR (400 MHz, CDCl$_3$) δ=7.67 (m, 9H), 7.61 (s, 2H), 6.82 (d, J=2.8 Hz, 1H), 6.72 (dd, J=9.0, 2.8 Hz, 1H), 6.64 (d, J=9.2 Hz, 1H), 5.08 (s, 2H), 4.58 (s, 2H), 2.22 (s, 3H). $^{19}$F-NMR (376 MHz, CDCl$_3$) δ=−62.4. No MS could be obtained.

Example A2

[4-(4-Methoxy-4''-trifluoromethoxy-[1,1';3',1'']terphenyl-5'-ylmethoxy)-2-methyl-phenoxy]-acetic acid

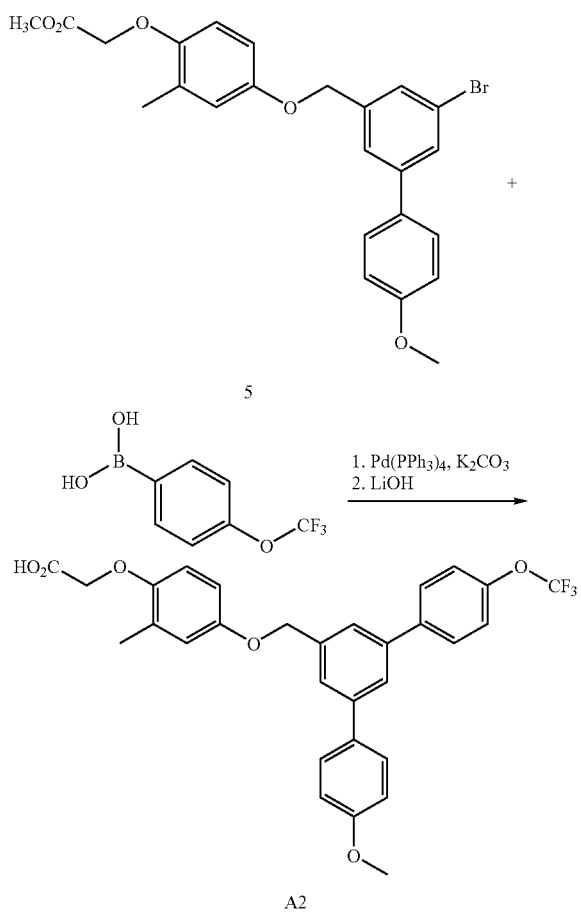

A2

5-Bromo-3-(4-ethoxy-3-methyl-phenoxymethyl)-4'-methoxy-biphenyl 15 (50 mg, 0.11 mmol) and 4-trifluoromethoxyphenylboronic acid (30 mg, 0.15 mmol, 1.3 equiv.) are dissolved in dioxane (0.5 mL). Potassium carbonate (38 mg, 0.27 mmol), water (0.05 mL) and ethanol (0.05 mL) are added, followed by tetrakis (triphenylphosphino)palladium (15.6 mg, 0.13 mmol). The mixture is stirred under nitrogen and subjected to microwave (170° C. for 10 min). Cooling, addition of 0.25 mL of aqueous 1N lithium hydroxide solution, and stirring for 3 hours at room temperature, followed by reversed-phase purification yielded [4-(4-methoxy-4"-trifluoromethoxy-[1,1';3',1"]terphenyl-5'-ylmethoxy)-2-methyl-phenoxy]-acetic acid A2. $^1$H-NMR (400 MHz, CDCl$_3$) δ=7.50 (m, 3H), 7.42 (m, 4H), 7.17 (d, J=8.0 Hz, 2H), 6.87 (d, J=8.0 Hz, 2H), 6.75 (d, J=2.8 Hz, 1H), 6.65 (dd, J=8.8, 2.8 Hz, 1H), 6.58 (d, J=8.8 Hz, 1H), 5.17 (s, 2H), 4.50 (s, 2H), 3.73 (s, 3H), 2.16 (s, 3H). $^{19}$F-NMR (376 MHz, CDCl$_3$) δ=−57.8. MS calculated for C$_{30}$H$_{26}$F$_3$O$_6$ (M+H$^+$) 539.17. found 539.0.

Example A3

[2-Methyl-4-(4"-trifluoromethoxy-4-trifluoromethyl-[1,1';3',1"]terphenyl-5'-ylmethoxy)-phenoxy]-acetic acid

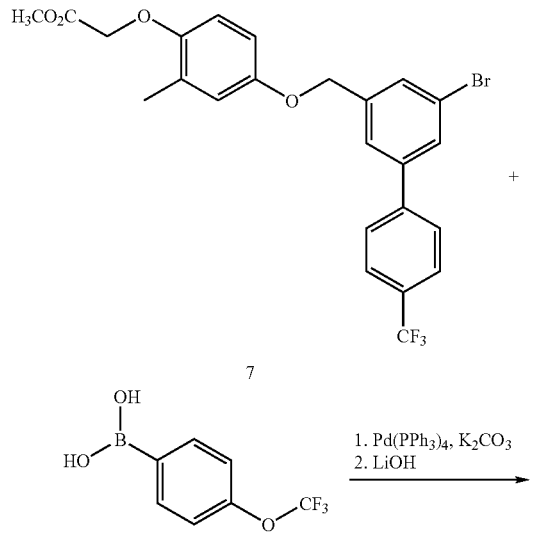

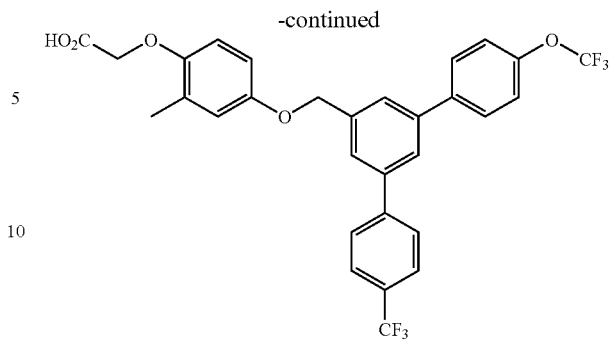

A3

4-(5-Bromo-4'-trifluoromethyl-biphenyl-3-ylmethoxy)-2-methyl-phenoxy]-acetic acid methyl ester 17 (25 mg, 0.05 mmol) and 4-trifluoromethoxyphenylboronic acid (15 mg, 0.07 mmol) are dissolved in dioxane (0.5 mL). Potassium carbonate (15 mg, 0.11 mmol), water (0.05 mL) and ethanol (0.05 mL) are added, followed by tetrakis(triphenylphosphino)palladium (10 mg, 0.009 mmol). The mixture is stirred under nitrogen and subjected to microwave (170° C. for 10 min). Cooling, addition of 0.25 mL of aqueous 1N lithium hydroxide solution, and stirring for 3 hours at room temperature, followed by reversed-phase purification yields [2-methyl-4-(4"-trifluoromethoxy-4-trifluoromethyl-[1,1';3',1"]terphenyl-5'-ylmethoxy)-phenoxy]-acetic acid A3. $^1$H-NMR (400 MHz, CDCl$_3$) δ=7.61 (m, 5H), 7.52 (m, 4H), 7.19 (d, J=8.8 Hz, 2H), 6.76 (d, J=2.8 Hz, 1H), 6.65 (dd, J=8.8, 2.8 Hz, 1H), 6.58 (d, J=8.8 Hz, 1H), 5.00 (s, 2H), 4.51 (s, 2H), 2.16 (s, 3H). $^{19}$F-NMR (376 MHz, CDCl$_3$) δ=−57.8 (s, 3F), −62.4 (s, 3F). MS calculated for C$_{30}$H$_{22}$F$_6$NaO$_5$ (M+Na$^+$) 599.1, found 598.8.

By repeating the procedures described in the above examples, using appropriate starting materials, the following compounds of Formula I, as identified in Table 1, are obtained.

TABLE 1

| Compound Number | Compound Structure | Physical Data $^1$H NMR 400 MHz (DMSO-d$_6$) and/or MS (m/z) |
|---|---|---|
| A4 | HO$_2$C-structure with terphenyl, methoxy groups | $^1$H-NMR (400 MHz, CDCl$_3$) δ = 7.54 (t, J=1.8 Hz, 1H), 7.45 (d, J= 8.8 Hz, 4H), 7.40 (d, J=1.8 Hz, 2H), 6.86 (d, J=8.8 Hz, 4H), 6.75 (d, J=2.8 Hz, 1H), 6.65 (dd, J= 8.8, 2.8 Hz, 1H), 6.58 (d, J=8.8 Hz, 1H), 4.97 (s, 2H), 4.50 (s, 2H), 3.73 (s, 6H), 2.15 (s, 3H). MS calculated for C$_{30}$H$_{29}$O$_6$ (M + H$^+$) 485.20, found 485.1. |

TABLE 1-continued

| Compound Number | Compound Structure | Physical Data $^1$H NMR 400 MHz (DMSO-$d_6$) and/or MS (m/z) |
| --- | --- | --- |
| A5 | 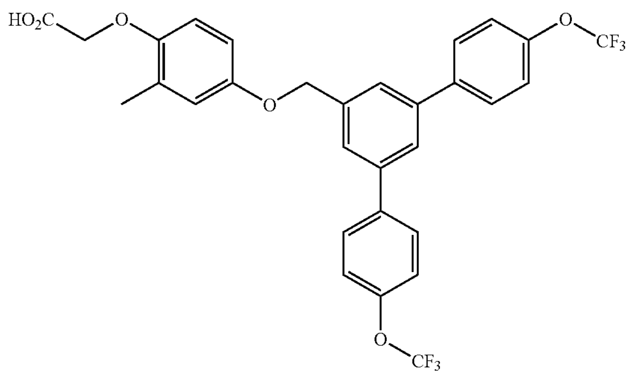 | $^1$H-NMR (400 MHz, CDCl$_3$) δ= 7.64-7.58 (m, 7H), 7.28 (d, J=8.8 Hz, 4H), 6.85 (d, J=2.8 Hz, 1H), 6.74 (dd, J=8.8, 2.8 Hz, 1H), 6.68 (d, J=8.8 Hz, 1H), 5.09 (s, 2H), 4.60 (s, 2H), 2.26 (s, 3H). $^{19}$F-NMR (376 MHz, CDCl$_3$) δ = −57.8. |
| A6 | 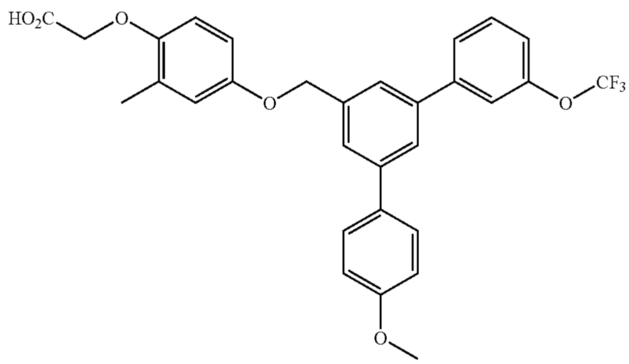 | $^1$H-NMR (400 MHz, CDCl$_3$) δ = 7.55 (s, 1H), 7.45 (m, 5H), 7.35 (m, 3H), 7.13 (m, 1H), 6.88 (d, J=8.0 Hz, 2H), 6.76 (d, J=2.8 Hz, 1H), 6.65 (dd, J=8.8, 2.8 Hz, 1H), 6.62 (d, J=8.8 Hz, 1H), 4.99 (s, 2H), 4.50 (s, 2H), 3.74 (s, 3H), 2.16 (s, 3H). $^{19}$F-NMR (376 MHz, CDCl$_3$) δ =−57.8. MS calculated for C$_{30}$H$_{26}$F$_3$O$_6$ (M + H$^+$) 539.17, found 539.1. |
| A7 | 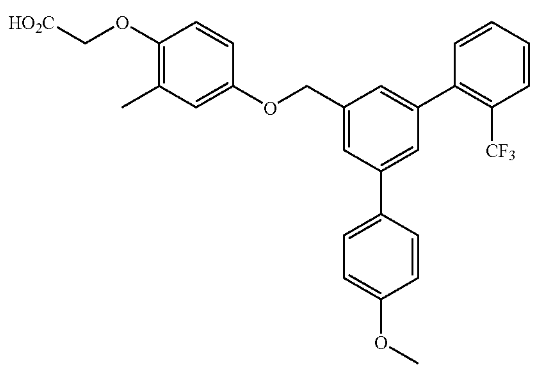 | $^1$H-NMR (400 MHz, CDCl$_3$) δ = 7.69 (d, J=8 Hz, 1H), 7.56 (s, 1H), 7.50 (m, 3H), 7.40 (m, 2H), 7.32 (d, J=7.6 Hz, 1H), 7.24 (s, 1H), 6.90 (d, J=8.0 Hz, 2H), 6.78 (d, J=2.8 Hz, 1H), 6.70 (dd, J=8.8, 2.8 Hz, 1H), 6.63 (d, J=8.8 Hz, 1H), 5.02 (s, 2H), 4.56 (s, 2H), 3.78 (s, 3H), 2.20 (s, 3H). $^{19}$F-NMR (376 MHz, CDCl$_3$) δ = −56.6. MS calculated for C$_{30}$H$_{26}$F$_3$O5 (M + H$^+$) 523.17, found 523.1. |
| A8 | 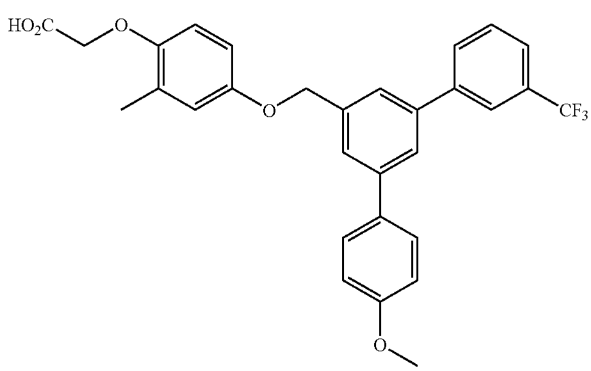 | $^1$H-NMR (400 MHz, CDCl$_3$) δ = 7.80 (s, 1H), 7.65 (d, J=8 Hz, 1H), 7.63 (s, 1H), 7.53 (m, 7H), 6.95 (d, J=8 Hz, 2H), 6.82 (d, J=2.8 Hz, 1H), 6.73 (dd, J=8.8, 2.8 Hz, 1H), 6.65 (d, J=8.8 Hz, 1H), 5.06 (s, 2H), 4.57 (s, 2H), 3.80 (s, 3H), 2.22 (s, 3H). $^{19}$F-NMR (376 MHz, CDCl$_3$) δ =−62.5. MS calculated for C$_{30}$H$_{26}$F$_3$O$_5$ (M +H$^+$) 523.17, found 523.0. |

TABLE 1-continued

| Compound Number | Compound Structure | Physical Data $^1$H NMR 400 MHz (DMSO-$d_6$) and/or MS (m/z) |
|---|---|---|
| A9 | 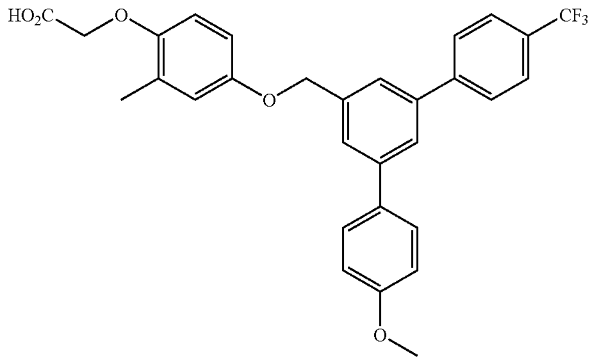 | $^1$H-NMR (400 MHz, CDCl$_3$) δ = 7.65 (m, 5H), 7.57 (s, 1H), 7.52 (m, 3H), 6.95 (d, J=8 Hz, 2H), 6.82 (d, J=2.8 Hz, 1H), 6.73 (dd, J=8.8, 2.8 Hz, 1H), 6.66 (d, J=8.8 Hz, 1H), 5.05 (s, 2H), 4.57 (s, 2H), 3.80 (s, 3H), 2.22 (s, 3H). $^{19}$FNMR (376 MHz, CDCl$_3$) δ = −62.4. MS calculated for C$_{30}$H$_{26}$F$_3$O$_5$ (M + H$^+$) 523.17, found 523.1. |
| A10 | 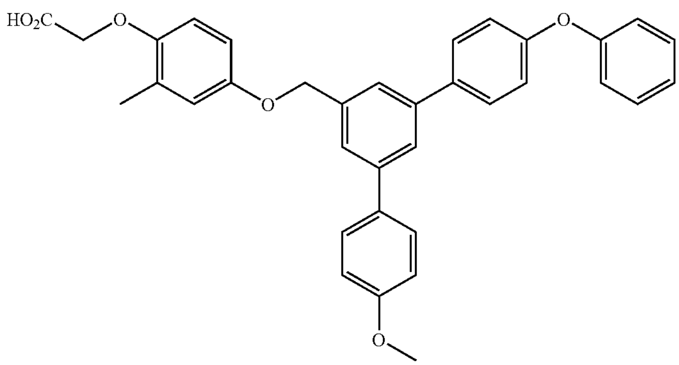 | $^1$H-NMR (400 MHz, CDCl$_3$) δ = 7.61 (t, J=1.6 Hz, 1H), 7.50 (m, 4H), 7.38 (m, 2H), 7.30 (m, 4H), 7.04 (m, 4H), 6.93 (d, J=8.8 Hz, 2H), 6.82 (d, J=2.8 Hz, 1H), 6.73 (dd, J=8.8, 2.8 Hz, 1H), 6.64 (d, J=8.8 Hz, 1H), 5.04 (s, 2H), 4.57 (s, 2H), 3.80 (s, 3H), 2.20 (s, 3H). MS calculated for C$_{35}$H$_{31}$O$_6$ (M + H$^+$) 547.21, found 547.2. |
| A11 | 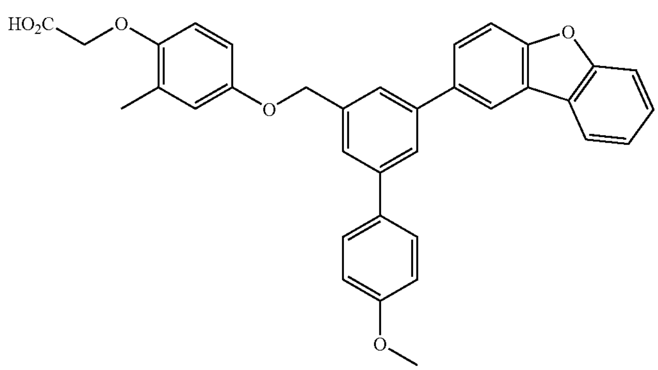 | $^1$H-NMR (400 MHz, CDCl$_3$) δ = 7.86 (m, 3H), 7.75 (s, 1H), 7.51 (m, 4H), 7.46 (d, J=8.0 Hz, 2H), 7.32 (m, 2H), 7.24 (m, 1H), 6.88 (d, J=8.8 Hz, 2H), 6.78 (d, J=2.8 Hz, 1H), 6.68 (dd, J=8.8, 2.8 Hz, 1H), 6.59 (d, J=8.8 Hz, 1H), 5.05 (s, 2H), 4.50 (s, 2H), 3.74 (s, 3H), 2.16 (s, 3H). MS calculated for C$_{35}$H$_{29}$O$_6$ (M + H$^+$) 545.20, found 545.2. |
| A12 | 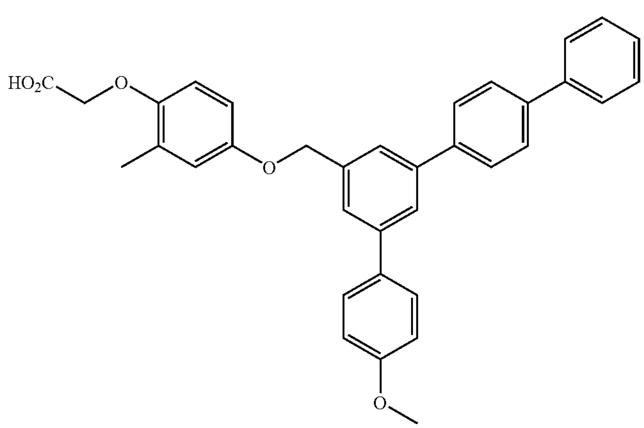 | $^1$H-NMR (400 MHz, CDCl$_3$) δ = 7.6-7.45 (m, 12H), 7.34 (m, 2H), 7.26 (m, 1H), 6.88 (d, J=8.8 Hz, 2H), 6.77 (d, J=2.8 Hz, 1H), 6.66 (dd, J=8.8, 2.8 Hz, 1H), 6.59 (d, J=8.8 Hz, 1H), 5.00 (s, 2H), 4.50 (s, 2H), 3.74 (s, 3H), 2.16 (s, 3H). MS calculated for C$_{35}$H$_{31}$O$_5$ (M + H$^+$) 531.21, found 531.2. |

TABLE 1-continued

| Compound Number | Compound Structure | Physical Data $^1$H NMR 400 MHz (DMSO-$d_6$) and/or MS (m/z) |
|---|---|---|
| A13 | 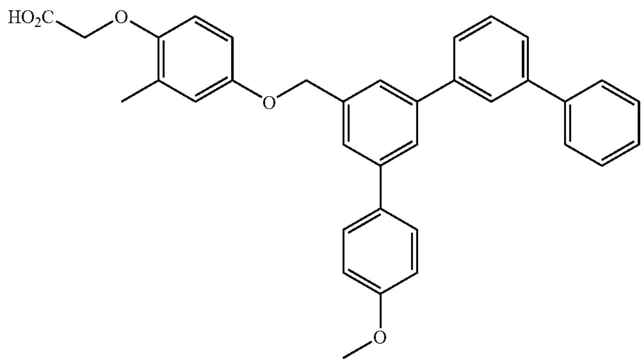 | $^1$H-NMR (400 MHz, CDCl$_3$) δ = 7.16 (t, J=2 Hz, 1H), 7.68 (t, J= 1.6 Hz, 1H), 7.64 (t, J=1.6 Hz, 1H), 7.52 (m, 4H), 7.46 (m, 2H), 7.40 (m, 1H), 7.33 (m, 2H), 7.24 (m, 2H), 6.87 (d, J=8.8 Hz, 2H), 6.76 (d, J=2.8 Hz, 1H), 6.66 (dd, J=8.8, 2.8 Hz, 1H), 6.58 (d, J= 8.8 Hz, 1H), 4.99 (s, 2H), 4.50 (s, 2H), 3.73 (s, 3H), 2.16 (s, 3H). MS calculated for C$_{35}$H$_{31}$O$_5$ (M + H$^+$) 531.21, found 531.2. |
| A14 | 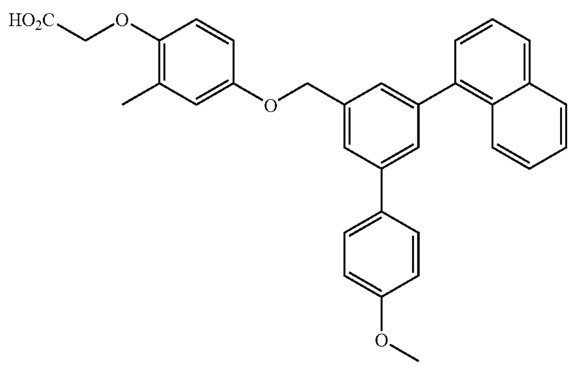 | $^1$H-NMR (400 MHz, CDCl$_3$) δ = 7.95 (m, 3H), 7.73 (s, 1H), 7.69 (s, 1H), 7.64 (d, J=8.8 Hz, 2H), 7.52 (m, 4H), 7.47 (m, 2H), 7.04 (d, J= 8.8 Hz, 2H), 6.93 (d, J=2.8 Hz, 1H), 6.82 (dd, J=8.8, 2.8 Hz, 1H), 6.75 (d, J=8.8 Hz, 1H), 5.14 (s, 2H), 4.68 (s, 2H), 3.90 (s, 3H), 2.33 (s, 3H). MS calculated for C$_{33}$H$_{29}$O$_5$ (M + H$^+$) 505.57, found 505.2. |
| A15 | 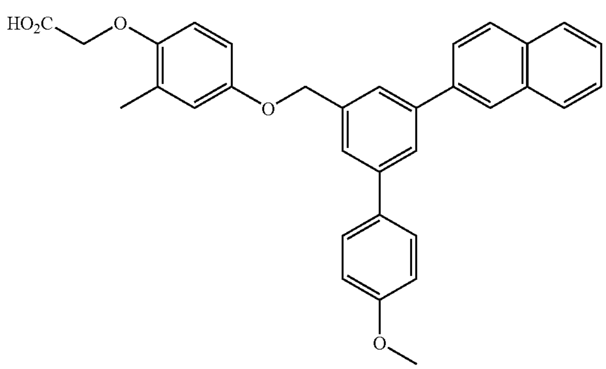 | $^1$H-NMR (400 MHz, CDCl$_3$) δ = 7.97 (s, 1H), 7.91 (s, 2H), 7.80 (m, 2H), 7.61 (m, 2H), 7.48 (m, 1H), 7.37 (m, 4H), 7.25 (m, 1H), 6.90 (d, J=8.8 Hz, 2H), 6.77 (d, J= 2.8 Hz, 1H), 6.67 (dd, J=8.8, 2.8 Hz, 1H), 6.59 (d, J=8.8 Hz, 1H), 5.01 (s, 2H), 4.50 (s, 2H), 3.74 (s, 3H), 2.16 (s, 3H). MS calculated for C$_{33}$H$_{29}$O$_5$ (M + H$^+$) 505.57, found 505.1. |
| A16 | 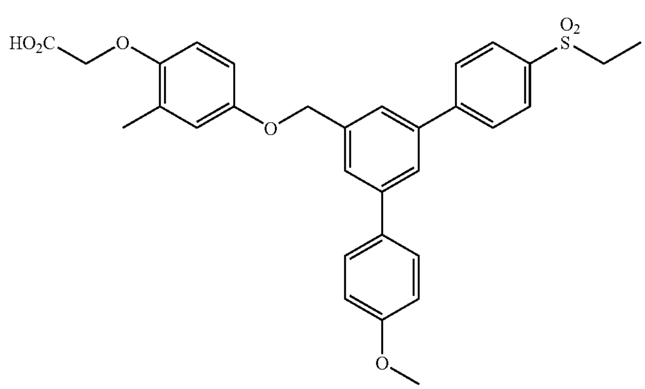 | $^1$H-NMR (400 MHz, CDCl$_3$) δ = 7.91 (d, J=8.4 Hz, 2H), 7.75 (d, J= 8.4 Hz, 2H), 7.65 (s, 1H), 7.58 (s, 2H), 7.51 (d, J=8.8 Hz, 2H), 6.94 (d, J=8.8 Hz, 2H), 6.81 (d, 2.8 Hz, 1H), 6.70 (dd, J=8.8, 2.8 Hz, 1H), 6.64 (d, J=8.8 Hz, 1H), 5.05 (s, 2H), 4.57 (s, 2H), 3.80 (s, 3H), 3.10 (q, J=7.6 Hz, 2H), 2.21 (s, 3H), 1.25 (t, J=7.6 Hz, 3H). MS calculated for C$_{31}$H$_{31}$O$_7$S (M + H$^+$) 547.18, found 547.2. |

TABLE 1-continued

| Compound Number | Compound Structure | Physical Data<br>¹H NMR 400 MHz (DMSO-d₆) and/or MS (m/z) |
| --- | --- | --- |
| A17 | 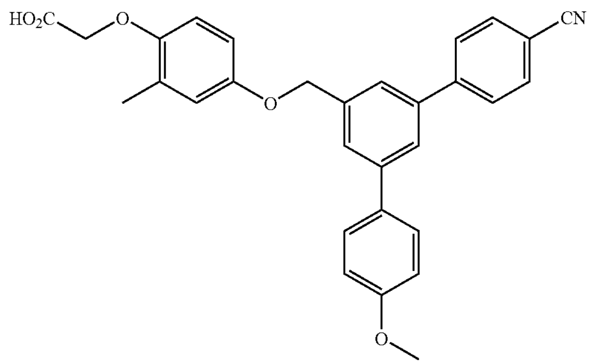 | ¹H-NMR (400 MHz, CDCl₃) δ = 7.61 (s, 4H), 7.55 (s, 1H), 7.45 (s, 2H), 7.43 (d, J=8.8 Hz, 2H), 6.87 (d, J=8.8 Hz, 2H), 6.74 (d, J= 2.8 Hz, 1H), 6.64 (dd, J=8.8, 2.8 Hz, 1H), 6.57 (d, J=8.8 Hz, 1H), 4.98 (s, 2H), 4.50 (s, 2H), 3.72 (s, 3H), 2.15 (s, 3H). MS calculated for C₃₁H₃₁O₇S (M + H⁺) 480.18, found 480.1. |
| A18 | 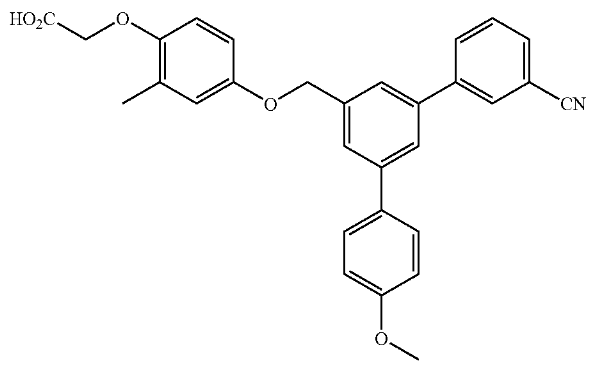 | ¹H-NMR (400 MHz, CDCl₃) δ = 7.79 (s, 1H), 7.73 (d, J=7.6 Hz, 1H), 7.50 (m, 3H), 7.44 (m, 4H), 6.87 (d, J=8.8 Hz, 2H), 6.76 (d, J=2.8 Hz, 1H), 6.65 (dd, J=8.8, 2.8 Hz, 1H), 6.58 (d, J=8.8 Hz, 1H), 4.99 (s, 2H), 4.51 (s, 2H), 3.74 (s, 3H), 2.16 (s, 3H). MS calculated for C₃₁H₃₁O₇S (M + H⁺) 480.18, found 480.1. |
| A19 | 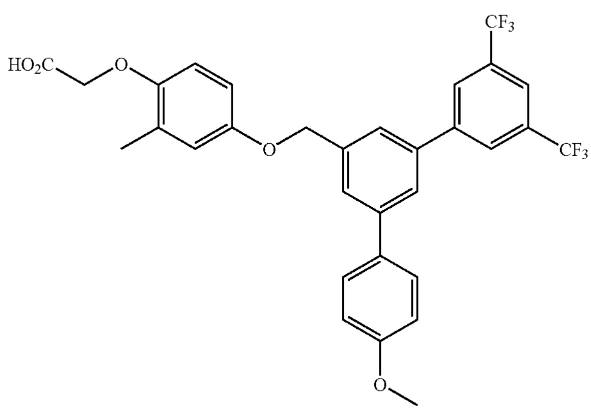 | ¹H-NMR (400 MHz, CDCl₃) δ = 7.92 (s, 2H), 7.75 (s, 1H), 7.55 (m, 2H), 7.61 (m, 3H), 6.88 (d, J=8.8 Hz, 2H), 6.76 (d, J=2.8 Hz, 1H), 6.65 (dd, J=8.8, 2.8 Hz, 1H), 6.58 (d, J=8.8 Hz, 1H), 5.00 (s, 2H), 4.51 (s, 2H), 3.74 (s, 3H), 2.15 (s, 3H). ¹⁹F-NMR (376 MHz, CDCl₃) δ = −62.7. |
| A20 | 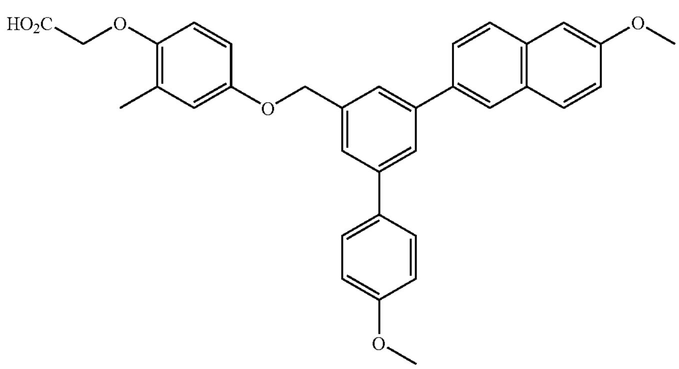 | ¹H-NMR (400 MHz, CDCl₃) δ = 7.90 (s, 1H), 7.69 (m, 3H), 7.63 (dd, J=8.4, 1.6 Hz, 1H), 7.56 (s, 1H), 7.48 (d, J=8.4 Hz, 2H), 7.46 (s, 1H), 7.06 (m, 2H), 6.88 (d, J=8.8 Hz, 2H), 6.77 (d, J=2.8 Hz, 1H), 6.68 (dd, J=8.8, 2.8 Hz, 1H), 6.59 (d, J=8.8 Hz, 1H), 5.00 (s, 2H), 4.50 (s, 2H), 3.83 (s, 3H), 3.74 (s, 3H), 2.16 (s, 3H). MS calculated for C₃₄H₃₁O₆ (M + H⁺) 535.20, found 535.2. |

TABLE 1-continued

| Compound Number | Compound Structure | Physical Data $^1$H NMR 400 MHz (DMSO-d$_6$) and/or MS (m/z) |
|---|---|---|
| A21 | 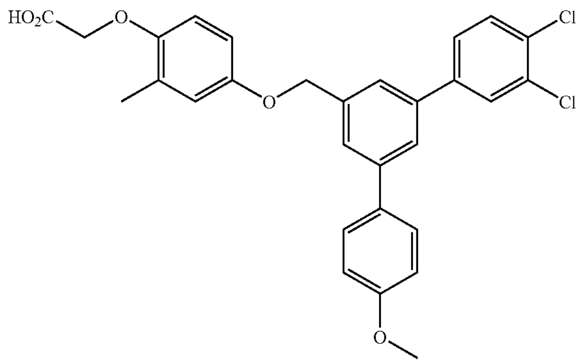 | $^1$H-NMR (400 MHz, CDCl$_3$) δ = 7.28 (d, J=2.0 Hz, 1H), 7.50 (t, J= 1.6 Hz, 1H), 7.47(t, J=1.0 Hz, 1H), 7.43 (d, J=8.8 Hz, 2H), 7.38 (m, 2H), 7.32 (dd, J=8.0, 2.0 Hz, 1H), 6.86 (d, J=8.8 Hz, 2H), 6.74 (d, J=2.8 Hz, 1H), 6.64 (dd, J= 8.8, 2.8 Hz, 1H), 6.57 (d, J=8.8 Hz, 1H), 4.96 (s, 2H), 4.50 (s, 2H), 3.73 (s, 3H), 2.15 (s, 3H). MS calculated for C$_{29}$H$_{25}$Cl$_2$O$_5$ (M + H$^+$) 523.10, found 523.0. |
| A22 | 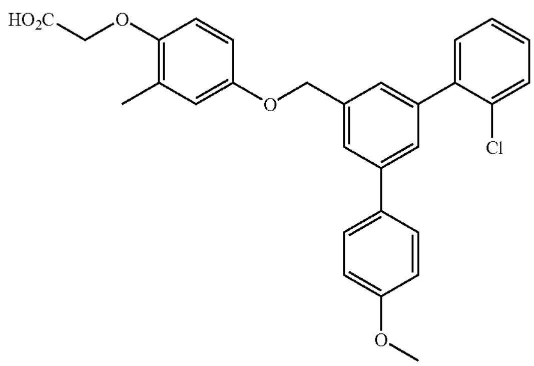 | $^1$H-NMR (400 MHz, CDCl$_3$) δ = 7.62 (s, 1H), 7.57 (m, 2H), 7.49 (dd, J=7.2, 1.6 Hz, 1H), 7.43 (s, 1H), 7.40 (dd, J=7.6, 2.0 Hz, 1H), 7.33 (m, 1H), 6.99 (d, J=8.8 Hz, 2H), 6.88 (d, J=2.8 Hz, 1H), 6.78 (dd, J=8.8, 2.8 Hz, 1H), 6.71 (d, J=8.8 Hz, 1H), 5.11 (s, 2H), 4.65 (s, 2H), 3.86 (s, 3H), 2.28 (s, 3H). MS calculated for C$_{29}$H$_{26}$ClO$_5$ (M + H$^+$) 489.14, found 489.0. |
| A23 | 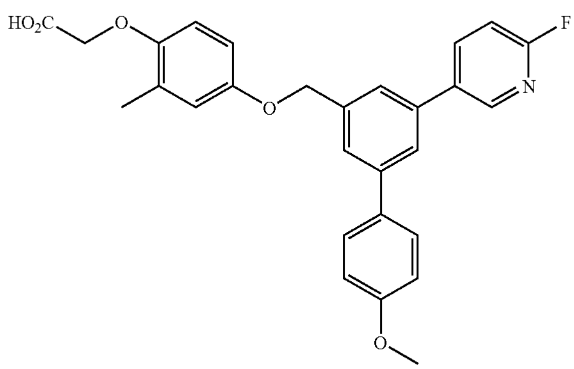 | $^1$H-NMR (400 MHz, CDCl$_3$) δ = 8.67 (s, 1H), 8.25 (td, J=8.0, 2.0 Hz, 1H), 7.81 (s, 2H), 7.77 (d, J= 8.8 Hz, 2H), 7.71 (s, 1H), 7.24 (d, J=7.6 Hz, 1H), 7.21 (d, J=8.8 Hz, 2H), 7.08 (d, J=2.8 Hz, 1H), 6.97 (dd, J=8.8, 2.8 Hz, 1H), 6.91 (d, J=8.8 Hz, 1H), 5.32 (s, 2H), 4.85 (s, 2H), 4.07 (s, 3H), 2.49 (s, 3H). $^{19}$F-NMR (376 MHz, CDCl$_3$) δ = −70.7. MS calculated for C$_{28}$H$_{25}$FNO$_5$ (M + H$^+$) 474.16, found 474.1. |
| A24 | 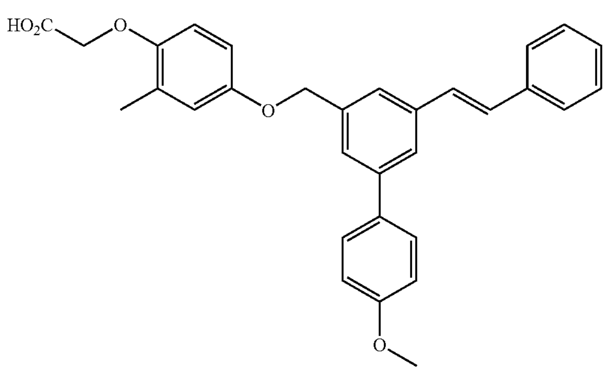 | $^1$H-NMR (400 MHz, CDCl$_3$) δ = 7.51 (s, 1H), 7.40 (m, 2H), 7.31 (m, 2H), 7.22 (m, 4H), 6.85 (m, 4H), 6.75 (d, J=2.8 Hz, 1H), 6.65 (dd, J=8.8, 2.8 Hz, 1H), 6.57 (m, 3H), 4.94 (s, 2H), 4.50 (s, 2H), 3.73 (s, 3H), 2.16 (s, 3H). MS calculated for C$_{31}$H$_{29}$O$_5$ (M + H$^+$) 481.20, found 481.1. |

TABLE 1-continued

| Compound Number | Compound Structure | Physical Data ¹H NMR 400 MHz (DMSO-$d_6$) and/or MS (m/z) |
|---|---|---|
| A25 | 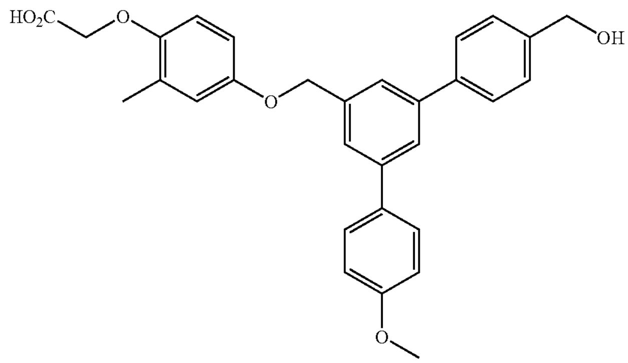 | ¹H-NMR (400 MHz, CDCl$_3$) δ = 7.67 (s, 1H), 7.58 (m, 4H), 7.53 (s, 2H), 6.99 (d, J=8.8 Hz, 4H), 6.88 (d, J=2.8 Hz, 1H), 6.78 (dd, J= 8.8, 2.8 Hz, 1H), 6.71 (d, J=8.8 Hz, 1H), 5.01 (s, 2H), 4.63 (s, 2H), 4.02 (s, 2H), 3.88 (s, 3H), 2.29 (s, 3H). MS calculated for C$_{30}$H$_{29}$O$_6$ (M + H⁺) 485.20, found 485.1. |
| A26 | 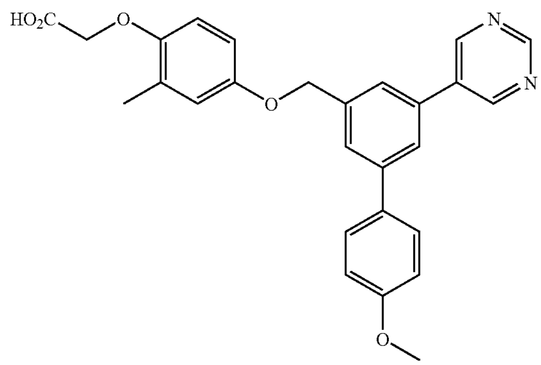 | ¹H-NMR (400 MHz, CDCl$_3$) δ = 9.32 (s, 1H), 9.10 (s, 2H), 7.72 (m, 1H), 7.59 (d, J=8.4 Hz, 2H), 7.53 (s, 2H), 7.04 (d, J=8.8 Hz, 1H), 6.88 (d, J=2.8 Hz, 18), 6.77 (m, 2H), 5.17 (s, 2H), 4.67 (s, 2H), 3.89 (s, 3H), 2.30 (s, 3H). MS calculated for C$_{27}$H$_{25}$N$_2$O$_5$ (M + H⁺) 457.17, found 457.1. |
| A27 | 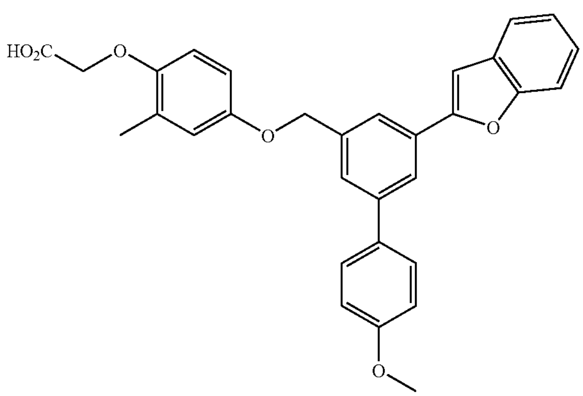 | ¹H-NMR (400 MHz, CDCl$_3$) δ = 7.81 (s, 1H), 7.72 (s, 1H), 7.50 (m, 3H), 7.41 (m, 2H), 7.18 (m, 2H), 6.97 (s, 1H), 6.88 (d, J=2.8 Hz, 1H), 6.77 (d, J=2.8 Hz, 1H), 6.66 (dd, J=8.8, 2.8 Hz, 1H), 6.58 (d, J= 8.8 Hz, 1H), 4.98 (s, 2H), 4.50 (s, 2H), 3.75 (s, 3H), 2.16 (s, 3H). MS calculated for C$_{31}$H$_{27}$O$_6$ (M + H⁺) 495.17, found 495.1. |
| A28 | 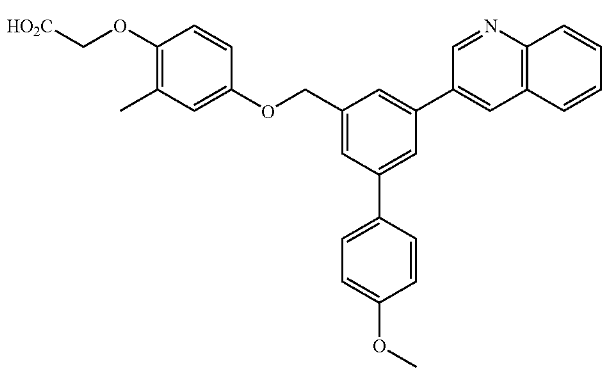 | ¹H-NMR (400 MHz, CDCl$_3$) δ = 9.31 (s, 1H), 8.86 (s, 1H), 8.53 (d, J=8.8 Hz, 1H), 8.08 (d, J=8.0 Hz, 1H), 7.97 (t, J=7.6 Hz, 1H), 7.83 (t, J=8.0 Hz, 1H), 7.73 (s, 1H), 7.68 (s, 1H), 7.53 (d, J=8.8 Hz, 2H), 7.51 (s, 1H), 6.96 (d, J= 8.8 Hz), 6.75 (d, J=2.8 Hz, 1H), 6.66 (dd, J=8.8, 2.8 Hz, 1H), 6.61 (d, J=8.8 Hz, 1H), 5.09 (s, 2H), 4.57 (s, 2H), 3.81 (s, 3H), 2.16 (s, 3H). MS calculated for C$_{32}$H$_{28}$NO$_5$ (M + H⁺) 506.2, found 506.0. |

TABLE 1-continued

| Compound Number | Compound Structure | Physical Data<br>¹H NMR 400 MHz (DMSO-d₆)<br>and/or MS (m/z) |
|---|---|---|
| A29 | 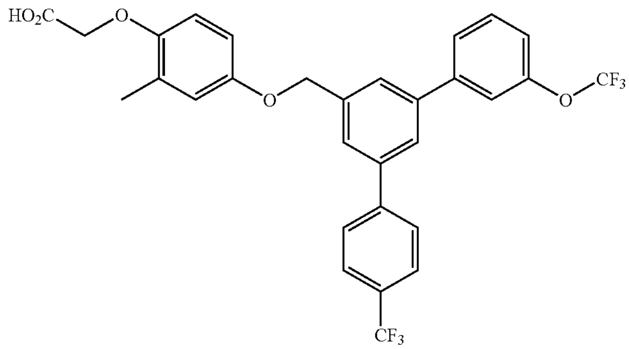 | ¹H-NMR (400 MHz, CDCl₃) δ = 7.74 (m, 5H), 1.66 (m, 2H), 7.57 (d, J=8.0 Hz, 1H), 7.50 (m, 3H), 7.25 (m, 2H), 6.76 (d, J=2.8 Hz, 1H), 6.65 (dd, J=8.8, 2.8 Hz, 1H), 6.58 (d, J=8.8 Hz, 1H), 5.14 (s, 2H), 4.65 (s, 2H), 2.29 (s, 3H). ¹⁹F-NMR (376 MHz, CDCl₃) δ = −57.6 (s, 3F), −62.4 (s, 3F). MS calculated for C₃₀H₂₂F₆NaO₅ (M + Na⁺) 599.1, found 598.8. |
| A30 | 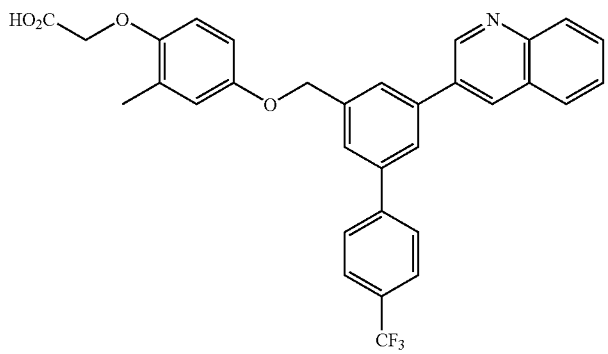 | ¹H-NMR (400 MHz, CD₃CN) δ = 9.37 (s, 1H), 9.14 (s, 1H), 8.33 (d, J=8.8 Hz, 1H), 8.19 (d, J=8.0 Hz, 1H), 8.03 (s, 1H), 7.98 (t, J=7.6 Hz, 1H), 7.89 (m, 3H), 7.83 (m, 2H), 7.76 (d, J=8.8 Hz), 6.86 (d, J=2.8 Hz, 1H), 6.75 (dd, J=8.8, 2.8 Hz, 1H), 6.68 (d, J=8.8 Hz, 1H), 5.14 (s, 2H), 4.54 (s, 2H), 2.15 (s, 3H). ¹⁹F-NMR (376 MHz, CDCl₃) δ = −62.5. MS calculated for C₃₂H₂₅F₃NO₄ (M + H⁺) 544.2, found 543.9. |
| A31 | 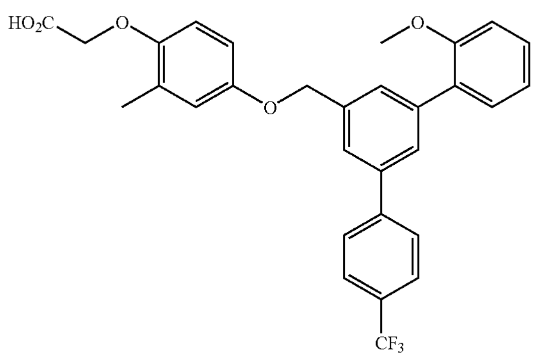 | ¹H-NMR (400 MHz, CDCl₃) δ = 7.72 (m, 5H), 7.62 (d, J=1.6 Hz, 1H), 7.34 (m, 2H), 7.07 (t, 7.2 Hz, 2H), 7.01 (d, J=8.0 Hz, 1H), 6.88 (d, J=2.8 Hz, 1H), 6.78 (dd, J=8.8, 2.8 Hz, 1H), 6.71 (d, J=8.8 Hz, 1H), 5.12 (s, 2H), 4.64 (s, 2H), 3.83 (s, 3H), 2.29 (s, 3H). MS calculated for C₃₀H₂₉F₆NO₅ (M + NH₄⁺) 540.2, found 539.9. |
| A32 | 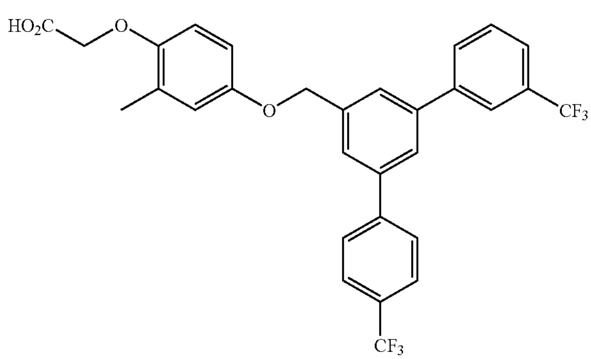 | ¹H-NMR (400 MHz, CDCl₃) δ = 7.74 (s, 1H), 7.69 (d, J=7.6 Hz, 1H), 7.60 (m, 5H), 7.53 (m, 3H), 7.46 (t, J=8.0 Hz, 1H), 6.76 (d, J=2.8 Hz, 1H), 6.65 (dd, J=8.8, 2.8 Hz, 1H), 6.58 (d, J=8.8 Hz, 1H), 5.01 (s, 2H), 4.51 (s, 2H), 2.15 (s, 3H). ¹⁹F-NMR (376 MHz, CDCl₃) δ = −62.42 (s, 3F), −62.53 (s, 3F). MS calculated for C₃₀H₂₂F₆NaO₄ (M + Na⁺) 583.1, found 582.8. |

TABLE 1-continued

| Compound Number | Compound Structure | Physical Data $^1$H NMR 400 MHz (DMSO-$d_6$) and/or MS (m/z) |
| --- | --- | --- |
| A33 | 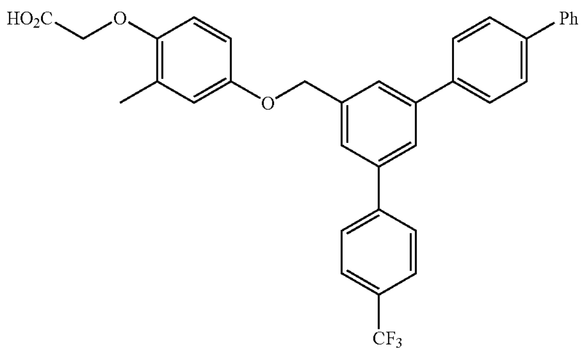 | $^1$H-NMR (400 MHz, CDCl$_3$) δ = 7.71 (m, 10H), 7.62 (m, 3H), 7.46 (t, J=7.6 Hz, 1H), 7.36 (t, J=7.2 Hz, 1H), 6.88 (d, J=2.8 Hz, 1H), 6.77 (dd, J=8.8, 2.8 Hz, 1H), 6.60 (d, J=8.8 Hz, 1H), 5.13 (s, 2H), 4.63 (s, 2H), 2.28 (s, 3H). $^{19}$F-NMR (376 MHz, CDCl$_3$) δ = −62.4. MS calculated for C$_{35}$H$_{27}$F$_3$NaO$_4$ (M + Na$^+$) 591.2, found 590.8. |
| A34 | 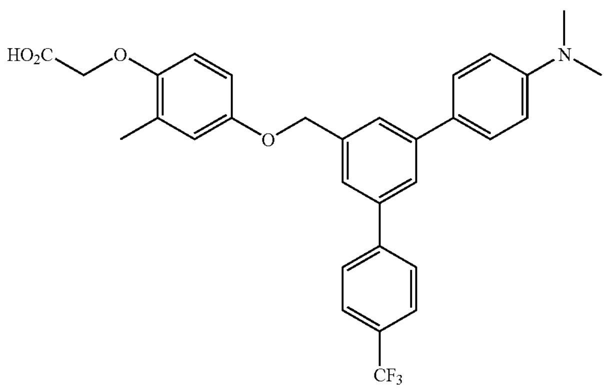 | $^1$H-NMR (400 MHz, CDCl$_3$) δ = 7.68 (m, 9H), 7.56 (s, 1H), 6.85 (d, J=2.8 Hz, 1H), 6.72 (m, 2H), 5.13 (s, 2H), 4.64 (s, 2H), 3.27 (s, 6H), 2.27 (s, 3H). $^{19}$F-NMR (376 MHz, CDCl$_3$) δ = −62.4 (s, 3F), −75.7 (br, s, 3F). MS calculated for C$_{31}$H$_{29}$F$_3$NO$_4$ (M + H$^+$) 536.2, found 535.9. |
| A35 | 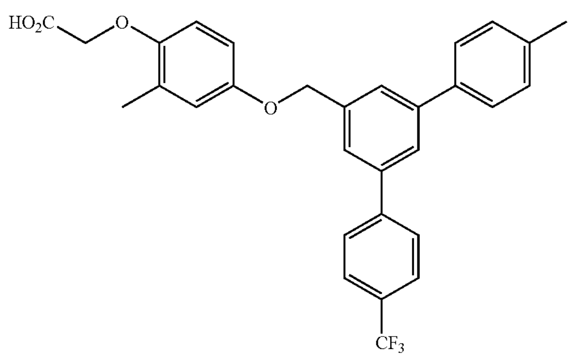 | $^1$H-NMR (400 MHz, CDCl$_3$) δ = 7.73 (m, 5H), 7.66 (s, 1H), 7.61 (s, 1H), 7.54 (d, J=8.0 Hz, 1H), 7.28 (d, J=8.0 Hz, 1H), 6.89 (d, J=2.8 Hz, 1H), 6.78 (dd, J=8.8, 2.8 Hz, 1H), 6.71 (d, J=8.8 Hz, 1H), 5.12 (s, 2H), 4.64 (s, 2H), 2.42 (s, 3H), 2.29 (s, 3H). $^{19}$F-NMR (376 MHz, CDCl$_3$) δ = −62.4. MS calculated for C$_{30}$H$_{25}$F$_3$NaO$_4$ (M + Na$^+$) 529.2, found 528.9. |
| A36 | 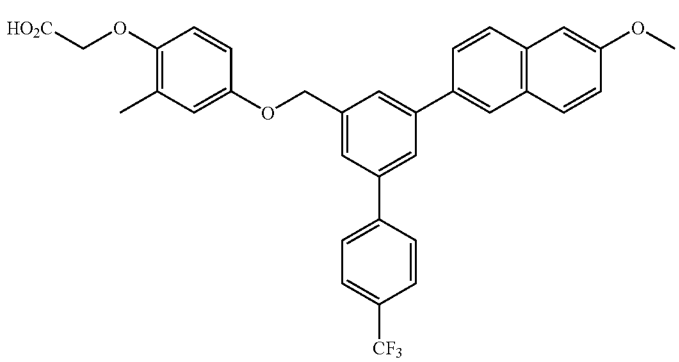 | $^1$H-NMR (400 MHz, CDCl$_3$) δ = 8.03 (s, 1H), 7.84 (m, 3H), 7.78 (m, 4H), 7.73 (m, 3H), 7.64 (s, 1H), 7.21 (m, 2H), 6.90 (d, J=2.8 Hz, 1H), 6.80 (dd, J=8.8, 2.8 Hz, 1H), 6.72 (d, J=8.8 Hz, 1H), 5.16 (s, 2H), 4.64 (s, 2H), 3.95 (s, 3H), 2.30 (s, 3H). $^{19}$F-NMR (376 MHz, CDCl$_3$) δ = −62.4. MS calculated for C$_{34}$H$_{28}$F$_3$O$_5$ (M + H$^+$) 573.2, found 572.9. |

TABLE 1-continued

| Compound Number | Compound Structure | Physical Data<br>$^1$H NMR 400 MHz (DMSO-$d_6$)<br>and/or MS (m/z) |
|---|---|---|
| A37 | 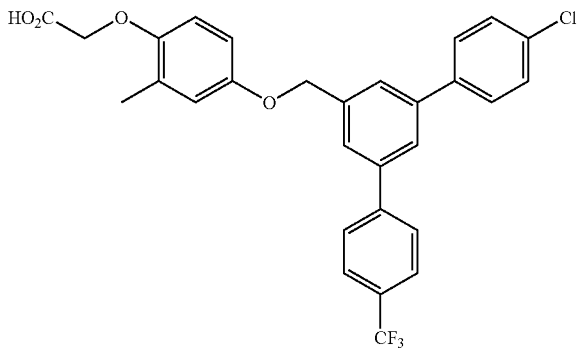 | $^1$H-NMR (400 MHz, CDCl$_3$) δ = 7.73 (m, 5H), 7.63 (d, J=1.6 Hz, 1H), 7.57 (d, J=8.4 Hz, 1H), 7.44 (d, J=8.4 Hz, 1H), 6.89(d, J= 2.8 Hz, 1H), 6.77 (dd, J=8.8, 2.8 Hz, 1H), 6.71 (d, J=8.8 Hz, 1H), 5.12 (s, 2H), 4.64 (s, 2H), 2.29 (s, 3H). $^{19}$F-NMR (376 MHz, CDCl$_3$) δ = −62.4. MS calculated for C$_{29}$H$_{22}$ClF$_3$NaO$_4$ (M + Na$^+$) 549.1, found 549.2. |
| A38 | 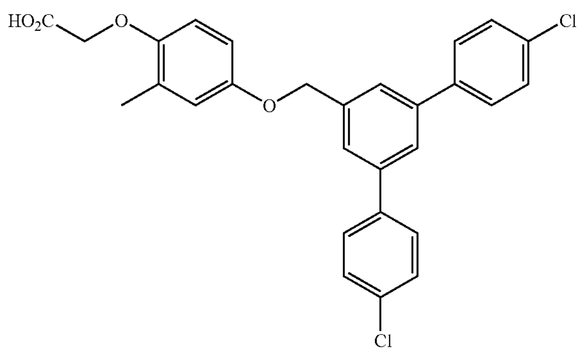 | $^1$H-NMR (400 MHz, CDCl$_3$) δ = 7.53 (t, J=1.6 Hz, 1H), 7.46 (d, J= 1.6 Hz, 2H), 7.43 (d, J=8.4 Hz, 4H), 7.30 (d, J=8.4 Hz, 4H), 6.76 (d, J=2.8 Hz, 1H), 6.65 (dd, J= 8.8, 2.8 Hz, 1H), 6.59 (d, J=8.8 Hz, 1H), 4.99 (s, 2H), 4.51 (s, 2H), 2.16 (s, 3H). MS calculated for C$_{28}$H$_{22}$Cl$_2$NaO$_4$ (M + Na$^+$) 515.1, found 515.1. |
| A39 | 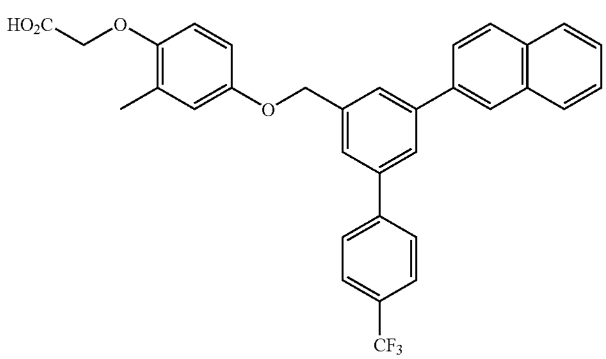 | $^1$H-NMR (400 MHz, CDCl$_3$) δ = 7.96 (s, 1H), 7.7 (m, 4H), 7.65 (m, 4H), 7.59 (m, 2H), 7.52 (s, 1H), 7.37 (m, 2H), 6.77 (d, J=2.8 Hz, 1H), 6.66 (dd, J=8.8, 2.8 Hz, 1H), 6.58 (d, J=8.8 Hz, 1H), 5.03 (s, 2H), 4.50 (s, 2H), 2.16 (s, 3H). MS calculated for C$_{33}$H$_{25}$F$_3$NaO$_4$ (M + Na$^+$) 565.2, found 564.9. |
| A40 | 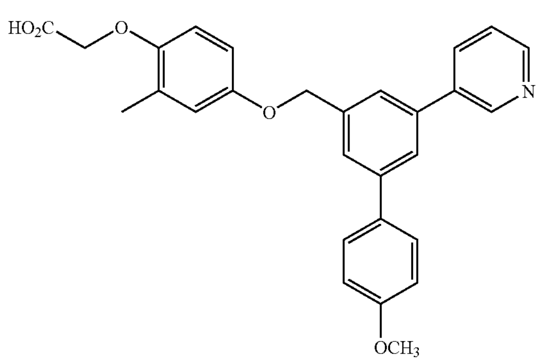 | $^1$H-NMR (400 MHz, CDCl$_3$) δ = 9.03 (s, 1H), 8.55 (m, 2H), 7.96 (m, 1H), 7.73 (s, 1H), 7.62 (s, 1H), 7.59 (d, J=8.8 Hz, 2H), 7.12 (s, 1H), 7.03 (d, J=8.8 Hz, 2H), 6.81 (dd, J=8.8, 2.8 Hz, 1H), 6.73 (d, J=8.8 Hz, 1H), 6.65 (d, J=2.8 Hz, 1H), 5.24 (s, 2H), 4.78 (s, 2H), 3.89 (s, 3H), 2.17 (s, 3H). MS calculated for C$_{28}$H$_{26}$NO$_5$ (M + H$^+$) 456.2, found 456.0. |

TABLE 1-continued

| Compound Number | Compound Structure | Physical Data $^1$H NMR 400 MHz (DMSO-$d_6$) and/or MS (m/z) |
|---|---|---|
| A41 | 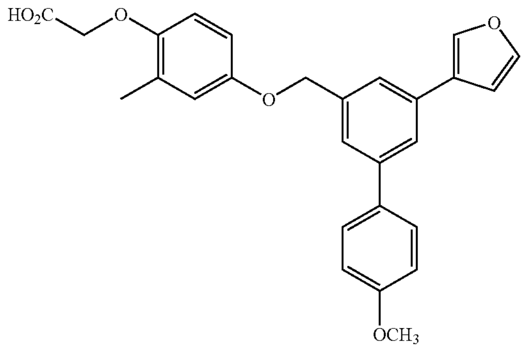 | $^1$H-NMR (400 MHz, CDCl$_3$) δ = 7.79 (s, 1H), 7.60 (s, 1H), 7.54 (d, J=8.8 Hz, 2H), 7.48 (m, 2H), 6.88 (d, J=2.8 Hz, 1H), 6.77 (dd, J=8.8, 2.8 Hz, 1H), 6.75 (m, 1H), 6.71 (d, J=8.8 Hz, 1H), 5.07 (s, 2H), 4.63 (s, 2H), 3.86 (s, 3H), 2.29 (s, 3H). MS calculated for C$_{27}$H$_{25}$O$_6$ (M + H$^+$) 445.1, found 445.0. |
| A42 | 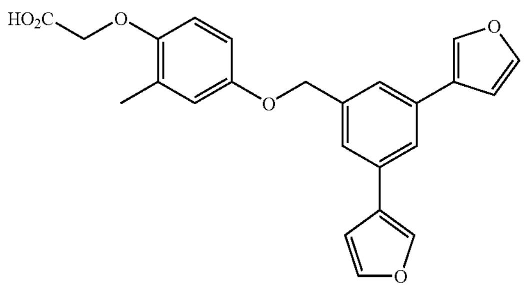 | $^1$H-NMR (400 MHz, CDCl$_3$) δ = 7.77 (s, 2H), 7.54 (s, 1H), 7.50 (s, 2H), 7.43 (s, 2H), 6.88 (d, J=2.8 Hz, 1H), 6.77 (dd, J=8.8, 2.8 Hz, 1H), 6.73 (m, 2H), 6.71 (d, J=8.8 Hz, 1H), 5.07 (s, 2H), 4.63 (s, 2H), 3.86 (s, 3H), 2.29 (s, 3H). MS calculated for C$_{24}$H$_{21}$O$_6$ (M + H$^+$) 405.1, found 405.0. |
| A43 | 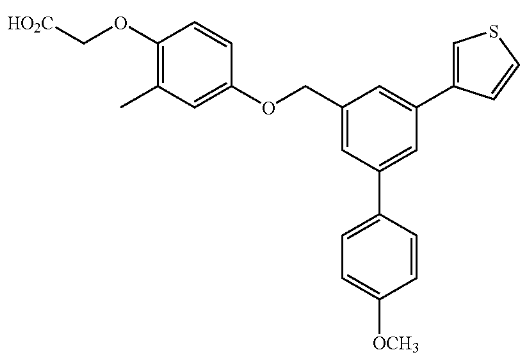 | $^1$H-NMR (400 MHz, CDCl$_3$) δ = 7.43 (m, 3H), 7.38 (m, 2H), 7.29 (m, 3H), 6.86 (d, J=8.4 Hz, 2H), 6.74 (d, J=2.8 Hz, 1H), 6.64 (dd, J=8.8, 2.8 Hz, 1H), 6.57 (d, J=8.8 Hz, 1H), 4.96 (s, 2H), 4.50 (s, 2H), 3.72 (s, 3H), 2.15 (s, 3H). MS calculated for C$_{27}$H$_{25}$O$_5$S (M + H$^+$) 461.1, found 460.9. |
| A44 | 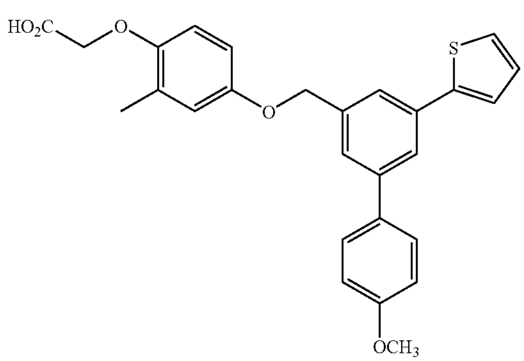 | $^1$H-NMR (400 MHz, CDCl$_3$) δ = 7.8-7.6 (m, 1H), 7.58 (6, J=8.0 Hz, 2H), 7.5 (m, 1H), 7.38 (m, 1H), 7.33 (m, 1H), 7.11 (m, 1H), 7.00 (d, J=8.0 Hz, 2H), 6.9 (m, 1H), 6.8 (m, 1H), 6.7 (m 1H), 5.08 (m, 2H), 4.59 (s, 2H), 3.85 (s, 3H), 2.29 (s, 3H) (two rotomers are present in a 2.3:1 ratio). MS calculated for C$_{27}$H$_{25}$O$_5$S (M + H$^+$) 461.1, found 460.9. |

TABLE 1-continued

| Compound Number | Compound Structure | Physical Data $^1$H NMR 400 MHz (DMSO-d$_6$) and/or MS (m/z) |
|---|---|---|
| A45 | 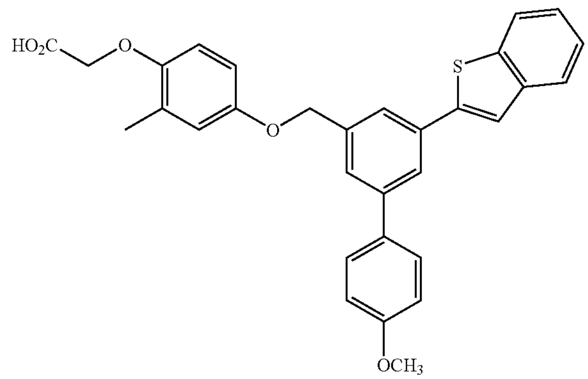 | $^1$H-NMR (400 MHz, CDCl$_3$) δ = 7.71 (m, 2H), 7.64 (m, 1H), 7.51 (s, 1H), 7.49 (s, 1H), 7.46 (d, J= 8.8 Hz, 1H), 7.44 (s, 1H), 7.22 (m, 2H), 6.88 (d, J=8.8 Hz, 1H), 6.76 (d, J=2.8 Hz, 1H), 6.66 (dd, J= 8.8, 2.8 Hz, 1H), 6.59 (d, J=8.8 Hz, 1H), 5.08 (m, 2H), 4.59 (s, 2H), 3.85 (s, 3H), 2.29 (s, 3H). MS calculated for C$_{31}$H$_{27}$O$_5$S (M + H$^+$) 511.1, found 510.9. |
| A46 | 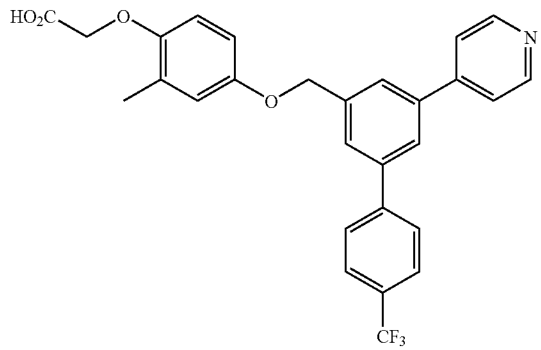 | $^1$H-NMR (400 MHz, CD$_3$CN) δ = 8.75 (br. s, 2H), 8.21 (br. s, 2H), 8.03 (s, 1H), 7.91 (s, 2H), 7.86 (d, J=5.2 Hz, 2H), 7.76 (d, J=5.2 Hz, 2H), 6.85 (d, J=2.8 Hz, 1H), 6.74 (dd, J=8.8, 2.8 Hz, 1H), 6.67 (d, J=8.8 Hz, 1H), 5.14 (s, 2H), 2.54 (s, 3H), 2.16 (s, 3H). $^{19}$F-NMR (376 MHz, CD$_3$CN) δ = −62.5, −76.0. MS calculated for C$_{28}$H$_{23}$F$_3$NO$_4$ (M + H$^+$) 494.2, found 593.9. |
| A47 | 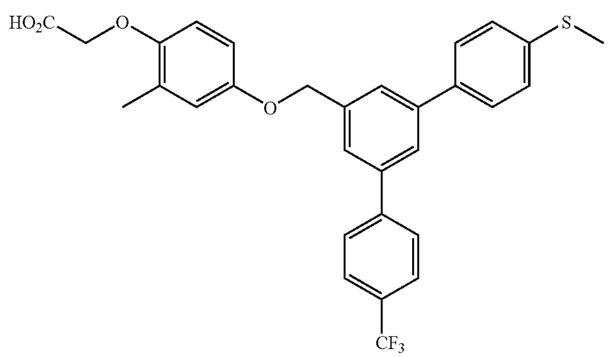 | $^1$H-NMR (400 MHz, CDCl$_3$) δ = 7.55 (m, 5H), 7.48 (s, 1H), 7.44 (s, 1H), 7.40 (d, J=8.2 Hz, 2H), 7.18 (d, J=8.2 Hz, 2H), 6.71 (d, J= 2.8 Hz, 1H), 6.61 (dd, J=8.8, 2.8 Hz, 1H), 6.55 (d, J=8.8 Hz, 1H), 4.95 (s, 2H), 4.47 (s, 2H), 2.36 (s, 3H), 2.12 (s, 3H). $^{19}$F-NMR (376 MHz, CDCl$_3$) δ = −62.4. MS calculated for C$_{30}$H$_{25}$F$_3$NaO$_4$S (M + H$^+$) 561.1, found 561.1. |
| A48 | 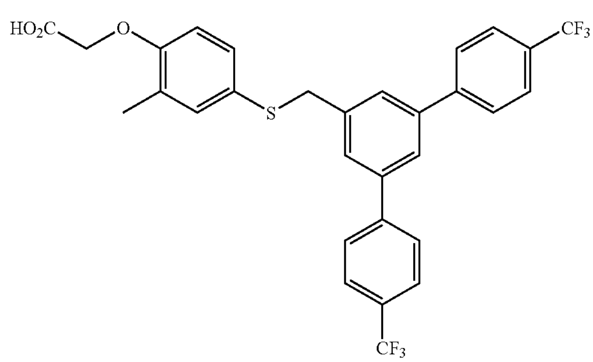 | $^1$H-NMR (400 MHz, CDCl$_3$) δ = 7.70 (m, 4H), 7.65 (m, 3H), 7.59 (d, J=8.0 Hz, 1H), 7.39 (d, J= 1.2 Hz, 2H), 7.17 (m, 3H), 6.63 (d, J=8.0 Hz, 1H), 4.66 (s, 2H), 4.11 (s, 2H), 2.22 (s, 3H); $^{19}$F-NMR (376 MHz, CDCl$_3$) δ = −62.38. MS calculated for C$_{30}$H$_{23}$F$_6$O$_3$S (M + H$^+$) 577.1, found 577.0. |

TABLE 1-continued

| Compound Number | Compound Structure | Physical Data $^1$H NMR 400 MHz (DMSO-$d_6$) and/or MS (m/z) |
|---|---|---|
| A49 | 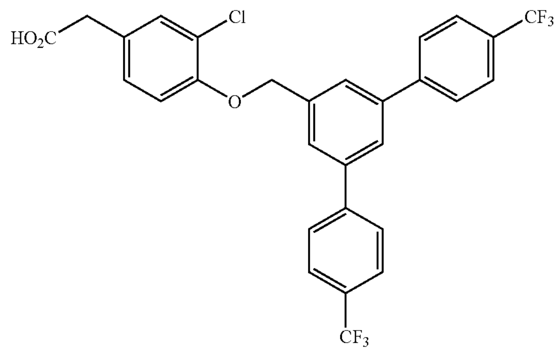 | $^1$H-NMR (400 MHz, CDCl$_3$) δ = 7.72 (m, 11H), 7.34 (d, J=2.4 Hz, 1H), 7.12 (dd, J=8.4, 2.4 Hz, 1H), 6.97 (d, J=8.4 Hz, 1H), 5.26 (s, 2H), 3.58 (s, 2H); $^{19}$F-NMR (376 MHz, CDCl$_3$) δ = −62.43. MS calculated for C$_{29}$H$_{20}$ClF$_6$O$_3$ (M + H$^+$) 565.1, found 565.0. |
| A50 | 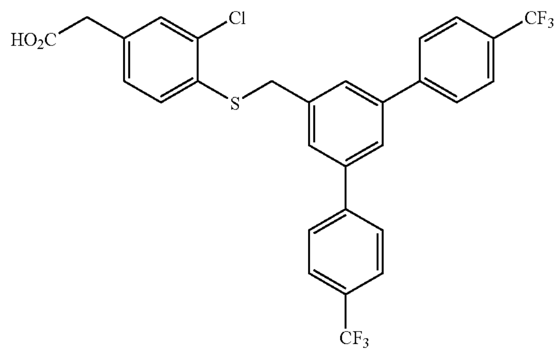 | $^1$H-NMR (400 MHz, CDCl$_3$) δ = 7.71 (m, 4H), 7.68 (m, 5H), 7.55 (d, J=1.6 Hz, 2H), 7.36 (d, J= 1.6 Hz, 1H), 7.27 (d, J=8.0 Hz, 1H), 7.10 (dd, J=8.0, 1.6 Hz, 1H), 4.26 (s, 2H), 3.60 (s, 2H); $^{19}$F-NMR (376 MHz, CDCl$_3$) δ = −62.40. MS calculated for C$_{29}$H$_{20}$ClF$_6$O$_2$S (M + H$^+$) 580.1, found 580.0. |

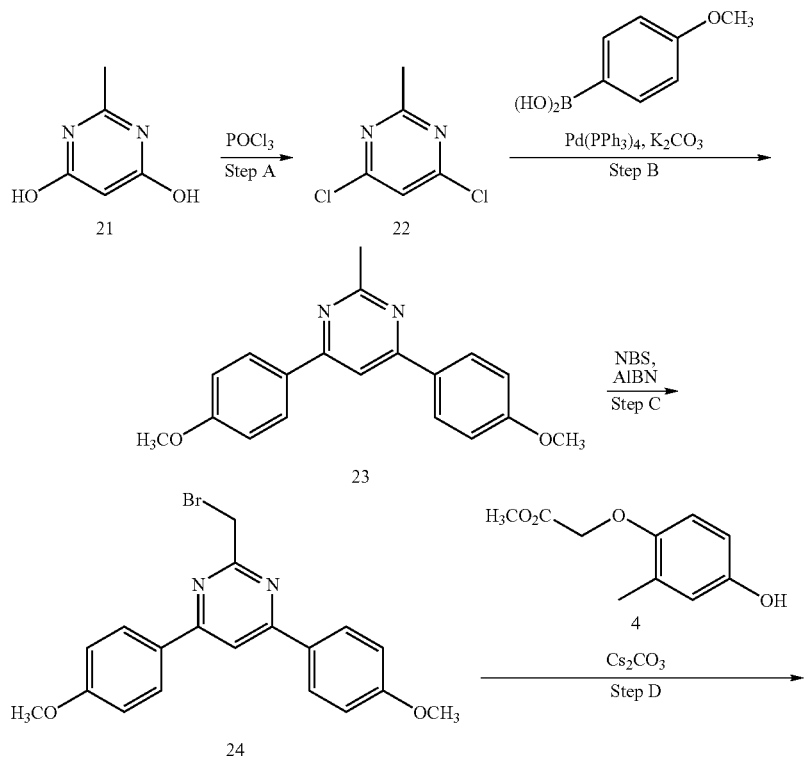

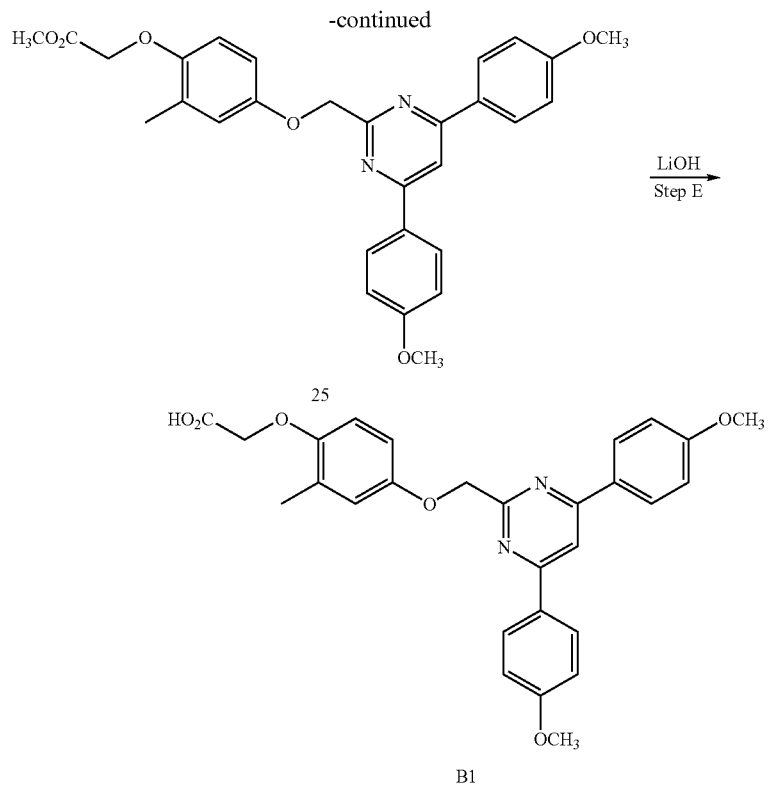

Example B1

{4-[4,6-Bis-(4-methoxy-phenyl)-pyrimidin-2-yl-methoxy]-2-methyl-phenoxy}-acetic acid Step A: 4,6-Dihydroxy-2-methylpyrimidine 21 (1.03 g, 8.1 mmol) is suspended in 2.5 mL phosphorus oxychloride (27.3 mmol). The mixture is heated to 95° C. for 18 hours. Upon cooling, the mixture is diluted with dichloromethane (100 mL) and filtered. It is then washed with water, saturated aqueous sodium bicarbonate and brine, then concentrated to yield 4,6-dichloro-2-methylpyrimidine 22 as a white powder. $^1$H-NMR (400 MHz, CDCl$_3$) δ=7.45 (s, 1H), 2.77 (s, 3H). MS calculated for C$_5$H$_5$Cl$_2$N$_2$ (M+H$^+$) 162.99. found 163.2.

Step B: The 4,6-dichloro-2-methylpyrimidine 22 (0.10 g, 0.6 mmol) is dissolved in dioxane (1 mL). 4-Methoxy-phenylboronic acid (0.32 g, 2.1 mmol) is added, followed by water (0.01 mL), ethanol (0.01 mL), potassium carbonate (0.40 g, 2.9 mmol), and tetrakistriphenyl-phosphino)palladium (0.13 g, 0.11 mmol). The mixture is stirred under nitrogen and subjected to microwave (170° C. for 5 min). The resulting orange suspension is filtered, the solids are washed with more dioxane, and the resulting solution is concentrated and purified by silica gel chromatography (5% to 25% ethyl acetate in hexanes) to yield the 4,6-bis-(4-methoxy-phenyl)-2-methyl-pyrimidine 23 as an oil. $^1$H-NMR (400 MHz, CDCl$_3$) δ=8.03 (d, J=8.8 Hz, 2H), 7.70 (s, 1H), 6.95 (d, J=8.8 Hz, 2H), 3.82 (s, 6H), 2.77 (s, 3H). MS calculated for C$_{19}$H$_{19}$N$_2$O$_2$ (M+H$^+$) 306.15, found 306.9.

Step C: 4,6-Bis-(4-methoxy-phenyl)-2-methyl-pyrimidine 23 (0.21 g, 0.7 mmol) is dissolved in 4 mL carbon tetrachloride. N-Bromo-succinimide (0.10 g, 0.56 mmol) is added and the mixture is heated to 75° C. with stirring. Solid 2,2'-azobisisobutyronitrile (AIBN) (0.01 g, 0.06 mmol) is added and the mixture is stirred at 75° C. for 24 hours. Cooling, diluting with dichloromethane, washing with water, saturated aqueous NaHCO$_3$, and brine, followed by drying over solid Na$_2$SO$_4$ and concentration yielded 2-bromomethyl-4,6-bis-(4-methoxy-phenyl)-pyrimidine 24 as an oil. It is used without further purification in the next step. $^1$H-NMR (400 MHz, CDCl$_3$) δ=8.02 (d, J=8.8 Hz, 2H), 7.69 (s, 1H), 6.94 (d, J=8.8 Hz, 2H), 3.82 (s, 2H).

Step D: (4-Hydroxy-2-methyl-phenoxy)-acetic acid methyl ester 4 (0.13 g, 0.66 mmol) is dissolved in dry acetonitrile (3 mL). Cesium carbonate (0.40 g, 1.2 mmol) is added, followed by 32-bromomethyl-4,6-bis-(4-methoxy-phenyl)-pyrimidine 24 from Step C above. The mixture is stirred under nitrogen at room temperature for 18 hours. The resulting suspension is filtered, the solids are washed with more acetonitrile, and the resulting clear solution is concentrated to yield crude {4-[4,6-Bis-(4-methoxy-phenyl)-pyrimidin-2-yl-methoxy]-2-methyl-phenoxy}-acetic acid methyl ester 25 as an oil. MS calculated for C$_{29}$H$_{29}$N$_2$O$_6$ (M+H$^+$) 500.19. found 500.1.

Step E: {4-[4,6-Bis-(4-methoxy-phenyl)-pyrimidin-2-yl-methoxy]-2-methyl-phenoxy}-acetic acid methyl ester 25 (0.14 g, 0.28 mmol) from Step D above is dissolved in dioxane (2 mL). Solid lithium hydroxide monohydrate (80 mg, 2.0 mmol) is added, followed by water (0.2 mL). After stirring at room temperature for 5 hours, the mixture is concentrated to dryness. Purification by reversed-phase HPLC afforded {4-[4,6-Bis-(4-methoxy-phenyl)-pyrimidin-2-ylmethoxy]-2-methyl-phenoxy}-acetic acid B1 as a solid. MS calculated for C$_{28}$H$_{27}$N$_2$O$_6$ (M+H$^+$) 487.18. found 487.2.

Example B2

{4-[2,6-Bis-(4-methoxy-phenyl)-pyrimidin-4-yl-methoxy]-2-methyl-phenoxy}-acetic acid

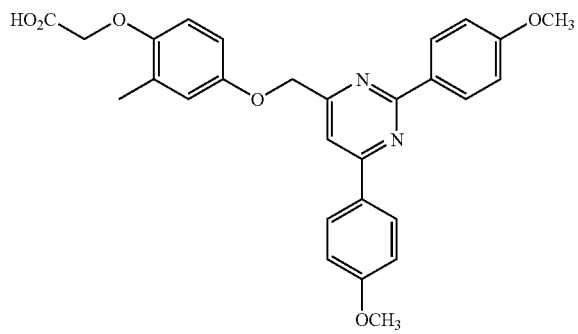

A similar procedure as for Example B1 is used for the preparation of example B2, using 2,4-dichloro-6-methylpyrimidine as the initial starting material instead of intermediate 22. $^1$H-NMR (400 MHz, CDCl$_3$) δ=8.49 (d, J=8.8 Hz, 2H), 8.19 (d, J=8.8 Hz, 2H), 7.71 (s, 1H), 7.01 (d, J=8.8 Hz, 4H), 6.88 (d, J=2.8 Hz, 1H), 6.74 (dd, J=8.8, 2.8 Hz, 1H), 6.67 (d, J=8.8 Hz, 1H), 5.19 (s, 2H), 4.60 (s, 2H), 3.89 (s, 6H), 2.26 (s, 3H). MS calculated for C$_{28}$H$_{27}$N$_2$O$_6$ (M+H$^+$) 487.18. found 487.2.

By repeating the procedures described in the above examples, using appropriate starting materials, the following compounds of Formula I, as identified in Table 2, are obtained.

TABLE 2

| Compound Number | Compound Structure | Physical Data $^1$H NMR 400 MHz (DMSO-d$_6$) and/or MS (m/z) |
|---|---|---|
| B3 | 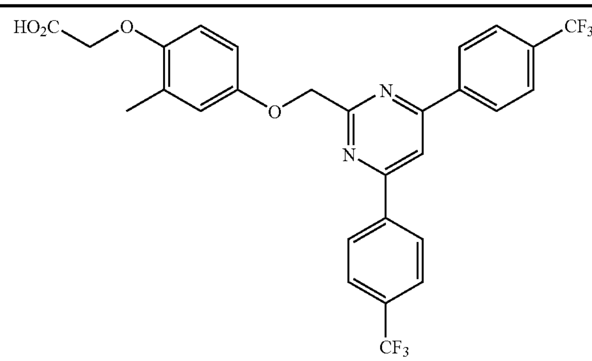 | $^1$H-NMR (400 MHz, CDCl$_3$) δ = 8.03 (d, J=8.4 Hz, 4H), 7.85 (s, 1H), 7.59 (d, J=8.4 Hz, 4H), 6.76 (d, J=2.8 Hz, 1H), 6.63 (dd, J=8.8, 2.8 Hz, 1H), 6.49 (d, J=8.8 Hz, 1H), 5.20 (s, 2H), 4.43 (s, 2H), 2.07 (s, 3H). $^{19}$F-NMR (376 MHz, CDCl$_3$) δ = −62.85. MS calculated for C$_{28}$H$_{21}$F$_6$N$_2$O$_4$ (M + H$^+$) 563.1, found 563.1. |
| B4 | 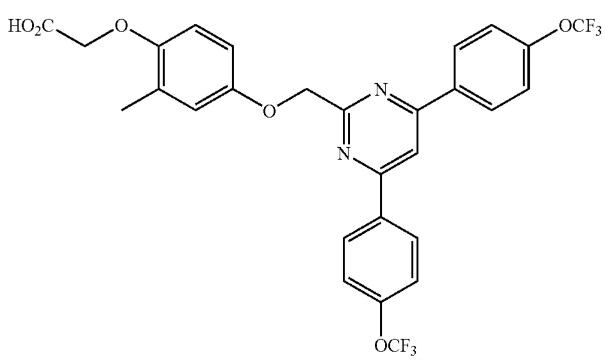 | $^1$H-NMR (400 MHz, CDCl$_3$) δ = 8.05 (d, J=8.4 Hz, 4H), 7.82 (s, 1H), 7.24 (d, J=8.4 Hz, 4H), 6.85 (d, J=2.8 Hz, 1H), 6.69 (dd, J=8.8, 2.8 Hz, 1H), 6.55 (d, J=8.8 Hz, 1H), 5.23 (s, 2H), 4.48 (s, 2H), 2.15 (s, 3H). $^{19}$F-NMR (376 MHz, CDCl$_3$) δ = −57.64. MS calculated for C$_{28}$H$_{21}$F$_6$N$_2$O$_6$ (M + H$^+$) 595.1, found 595.1. |
| B5 | 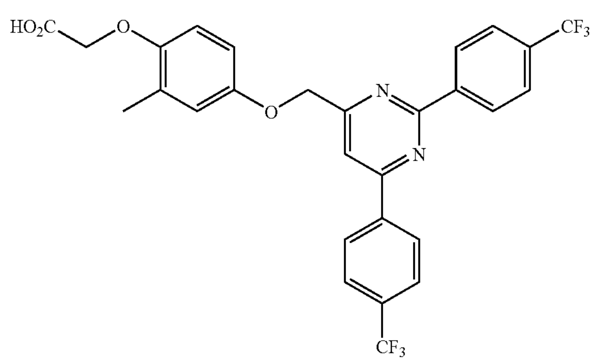 | $^1$H-NMR (400 MHz, CDCl$_3$) δ = 8.68 (d, J=8.4 Hz, 2H), 8.31 (d, J=8.4 Hz, 2H), 7.91 (s, 1H), 7.77 (m, 4H), 6.91 (d, J=2.8 Hz, 1H), 6.78 (dd, J=8.8, 2.8 Hz, 1H), 6.70 (d, J=8.8 Hz, 1H), 5.23 (s, 2H), 4.63 (s, 2H), 2.28 (s, 3H). $^{19}$F-NMR (376 MHz, CDCl$_3$) δ = −62.70 (s, 3F), −62.82 (s, 3F). MS calculated for C$_{28}$H$_{21}$F$_6$N$_2$O$_4$ (M + H$^+$) 563.1, found 563.2. |

TABLE 2-continued

| Compound Number | Compound Structure | Physical Data<br>$^1$H NMR 400 MHz (DMSO-$d_6$)<br>and/or MS (m/z) |
|---|---|---|
| B6 | [structure: HO$_2$C-CH$_2$-O-(methylphenyl)-O-CH$_2$-pyrimidine substituted with two 4-OCF$_3$-phenyl groups] | $^1$H-NMR (400 MHz, CDCl$_3$) δ = 8.64 (d, J=8.4 Hz, 2H), 8.27 (d, J= 8.4 Hz, 2H), 7.83 (s, 1H), 7.37 (m, 4H), 6.92 (d, J=2.8 Hz, 1H), 6.80 (dd, J=8.8, 2.8 Hz, 1H), 6.73 (d, J=8.8 Hz, 1H), 5.23 (s, 2H), 4.65 (s, 2H), 2.30 (s, 3H). $^{19}$F-NMR (376 MHz, CDCl$_3$) δ = −57.58 (s, 3F), −57.64 (s, 3F). MS calculated for $C_{28}H_{21}F_6N_2O_6$ $(M+H^+)$ 595.1, found 595.0. |

Transcriptional Assay

Transfection assays are used to assess the ability of compounds of the invention to modulate the transcriptional activity of the PPARs. Briefly, expression vectors for chimeric proteins containing the DNA binding domain of yeast GAL4 fused to the ligand-binding domain (LBD) of either PPARδ, PPARα or PPARγ are introduced via transient transfection into mammalian cells, together with a reporter plasmid where the luciferase gene is under the control of a GAL4 binding site. Upon exposure to a PPAR modulator, PPAR transcriptional activity varies, and this can be monitored by changes in luciferase levels. If transfected cells are exposed to a PPAR agonist, PPAR-dependent transcriptional activity increases and luciferase levels rise.

293T human embryonic kidney cells (8×10$^6$) are seeded in a 175 cm$^2$ flask a day prior to the start of the experiment in 10% FBS, 1% Penicillin/Streptomycin/Fungizome, DMEM Media. The cells are harvested by washing with PBS (30 ml) and then dissociating using trypsin (0.05%; 3 ml). The trypsin is inactivated by the addition of assay media (DMEM, CA-dextran fetal bovine serum (5%). The cells are spun down and resuspended to 170,000 cells/ml. A Transfection mixture of GAL4-PPAR LBD expression plasmid (1 μg), UAS-luciferase reporter plasmid (1 μg), Fugene (3:1 ratio; 6 μL) and serum-free media (200 μL) was prepared and incubated for 15-40 minutes at room temperature. Transfection mixtures are added to the cells to give 0.16M cells/mL, and cells (50 μl/well) are then plated into 384 white, solid-bottom, TC-treated plates. The cells are further incubated at 37° C., 5.0% CO$_2$ for 5-7 hours. A 12-point series of dilutions (3 fold serial dilutions) are prepared for each test compound in DMSO with a starting compound concentration of 10 μM. Test compound (500 nl) is added to each well of cells in the assay plate and the cells are incubated at 37° C., 5.0% CO$_2$ for 18-24 hours. The cell lysis/luciferase assay buffer, Bright-Glo™ (25%; 25 μl; Promega), is added to each well. After a further incubation for 5 minutes at room temperature, the luciferase activity is measured.

Raw luminescence values are normalized by dividing them by the value of the DMSO control present on each plate. Normalized data is analyzed and dose-response curves are fitted using Prizm graph fitting program. EC50 is defined as the concentration at which the compound elicits a response that is half way between the maximum and minimum values. Relative efficacy (or percent efficacy) is calculated by comparison of the response elicited by the compound with the maximum value obtained for a reference PPAR modulator.

Compounds of Formula I, in free form or in pharmaceutically acceptable salt form, exhibit valuable pharmacological properties, for example, as indicated by the in vitro tests described in this application. Compounds of the invention preferably have an EC50 for PPARδ of less than 1 μM, more preferably less than 500 nm, more preferably less than 100 nM. Compounds of the invention are at least 100-fold selective for PPARδ over PPARγ.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:
1. A compound of Formula Ia:

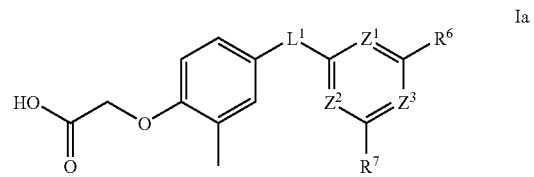

Ia in which
Z$^1$, Z$^2$ and Z$^3$ are members independently selected from CH and N;
L$^1$ is selected from —CH$_2$O—, —OCH$_2$—, —CH$_2$S— and —SCH$_2$—;
R$^6$ and R$^7$ are independently selected from —R$^{10}$ and —YR$^{10}$; wherein Y is propenylene; and R$^{10}$ is selected from phenyl, biphenyl, naphthyl, benzo[b]furanyl, pyridinyl, pyrimidinyl, dibenzo-furan-2-yl, furanyl, benzo[b]thiophene, thienyl and quinolinyl; wherein any aryl or heteroaryl of R$^{10}$ is optionally substituted with 1 to 3 radicals independently selected from halo, cyano, methyl, hydroxy-methyl, methyl-sulfanyl, methoxy, trifluoromethyl, trifluoromethoxy, phenoxy, ethyl-sulfonyl and dimethylamino.

2. The compound of claim 1 of Formula Ib:

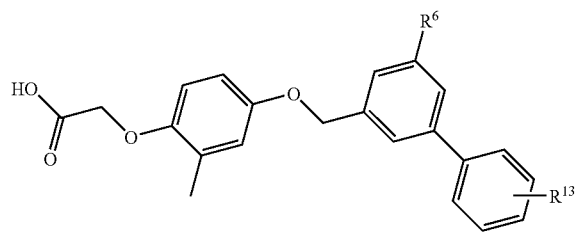

Ib in which R⁶ is selected from —R¹⁰ and —YR¹⁰; wherein Y is propenylene; and R¹⁰ is selected from phenyl, biphenyl, naphthyl, benzo[b]furanyl, pyridinyl, pyrimidinyl, dibenzo-furan-2-yl, furanyl, benzo[b]thiophene, thienyl and quinolinyl; wherein any aryl or heteroaryl of R¹⁰ is optionally substituted with 1 to 3 radicals independently selected from halo, cyano, methyl, hydroxy-methyl, methyl-sulfanyl, methoxy, trifluoromethyl, trifluoromethoxy, phenoxy, ethyl-sulfonyl and dimethylamino; and R¹³ is selected from methoxy, trifluoromethyl and trifluoromethoxy.

3. A compound of claim 1 selected from: [4-(3,5-Bis(4-trifluoromethylphenyl)-benzyloxy)-2-methyl-phenoxy]-acetic acid; [4-(4-Methoxy-4''-trifluoromethoxy-[1,1'; 3',1'']terphenyl-5'-ylmethoxy)-2-methyl-phenoxy]-acetic acid; [2-Methyl-4-(4''-trifluoromethoxy-4-trifluoromethyl-[1,1'; 3',1'']terphenyl-5'-ylmethoxy)-phenoxy]-acetic acid; {4-[4,6-Bis-(4-methoxy-phenyl)-pyrimidin-2-ylmethoxy]-2-methyl-phenoxy}-acetic acid; and {4-[2,6-Bis-(4-methoxy-phenyl)-pyrimidin-4-ylmethoxy]-2-methyl-phenoxy}-acetic acid.

4. A compound of claim 1 selected from:

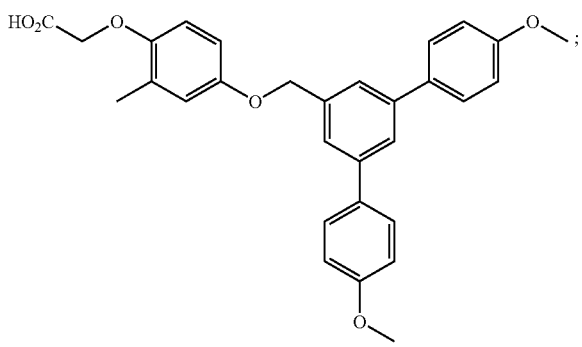

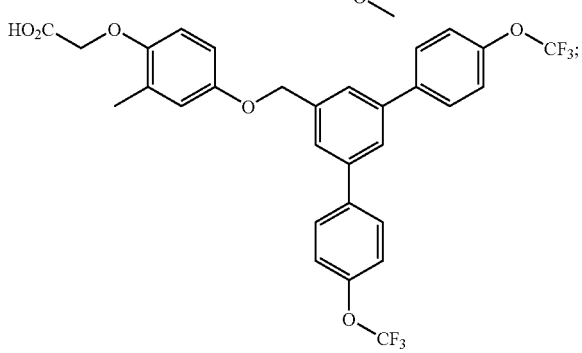

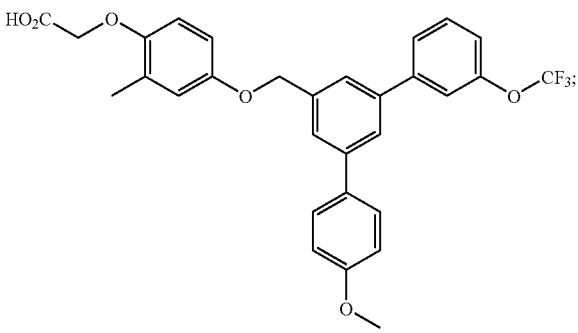

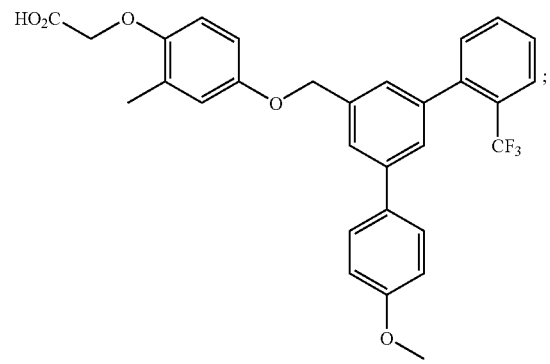

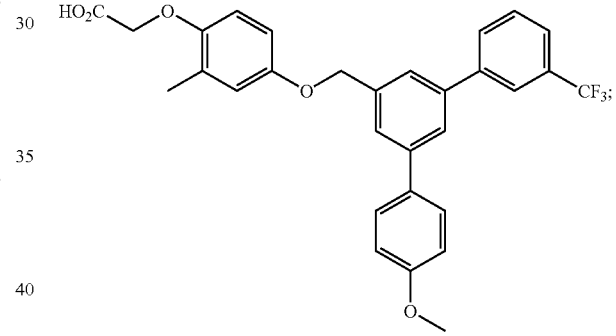

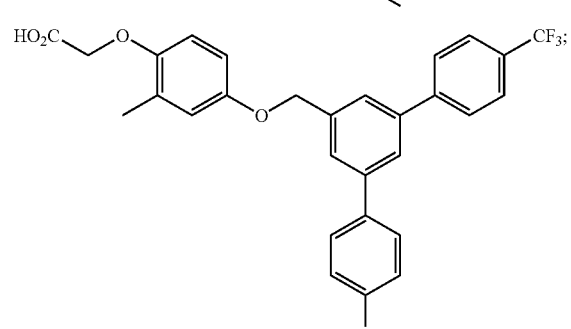

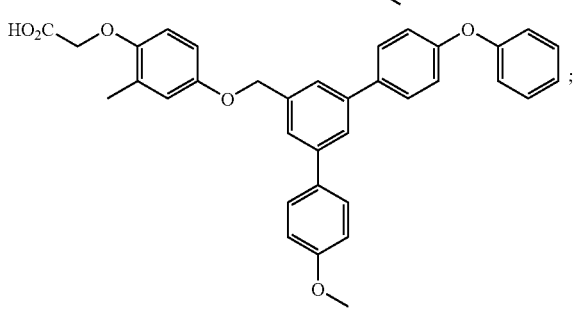

57
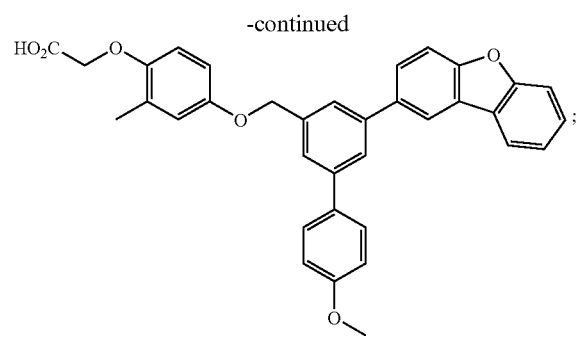
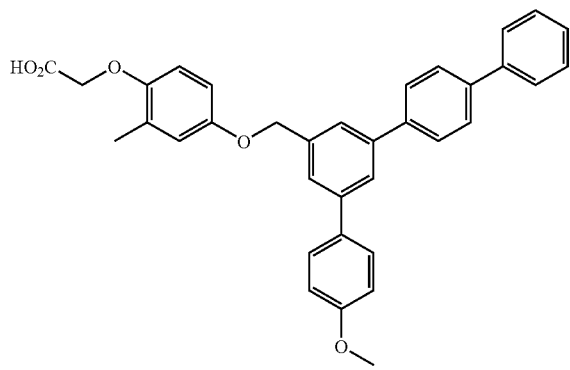
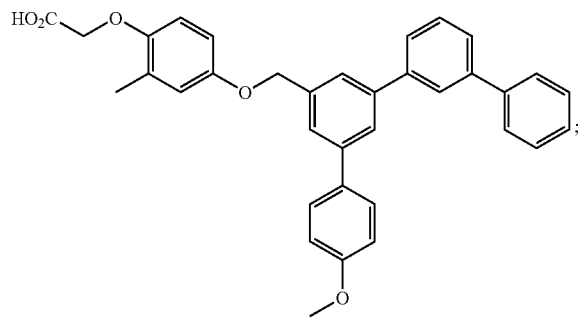
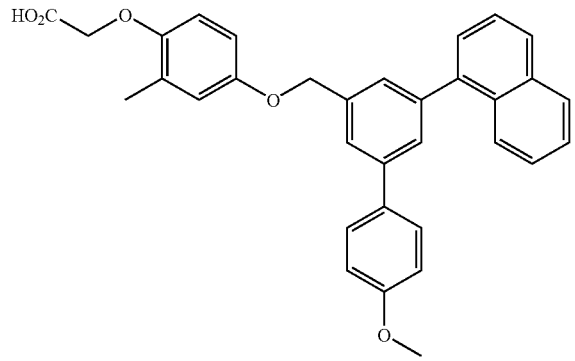
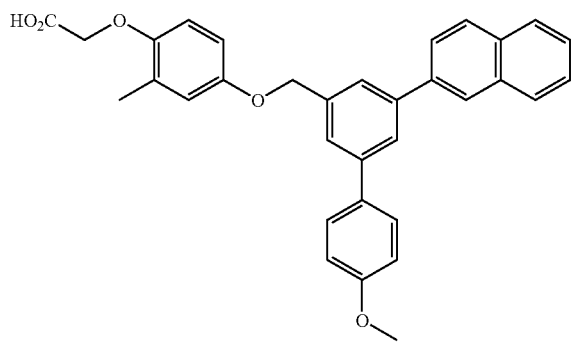
58
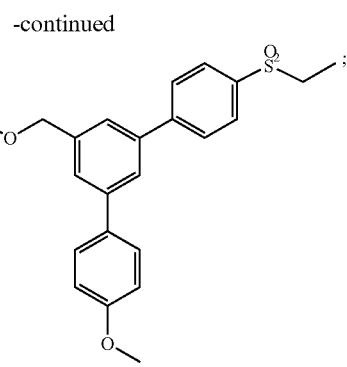
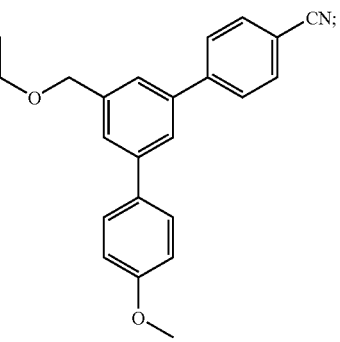
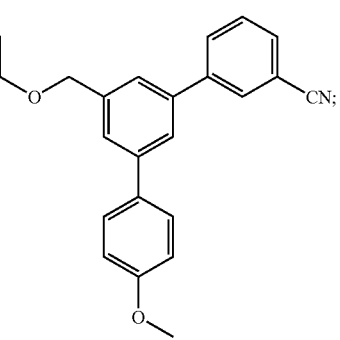
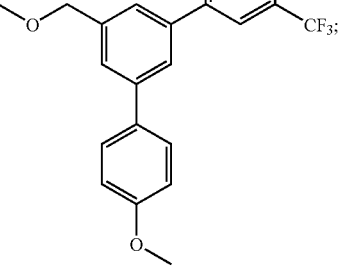
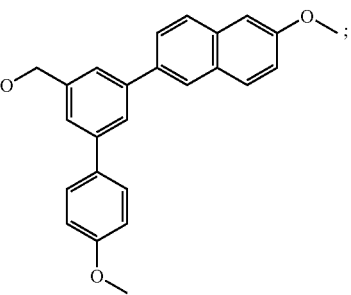

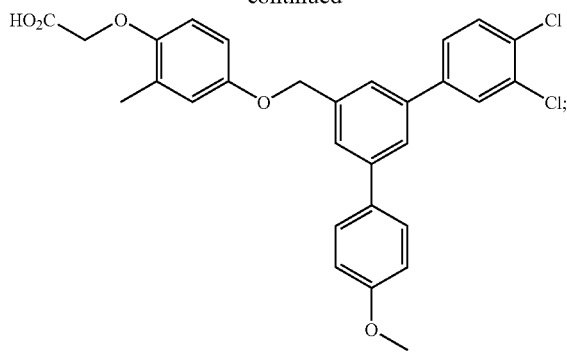
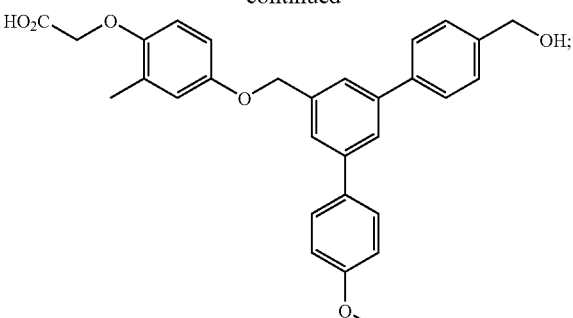
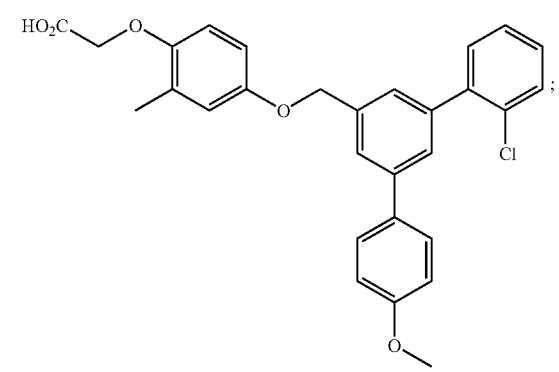
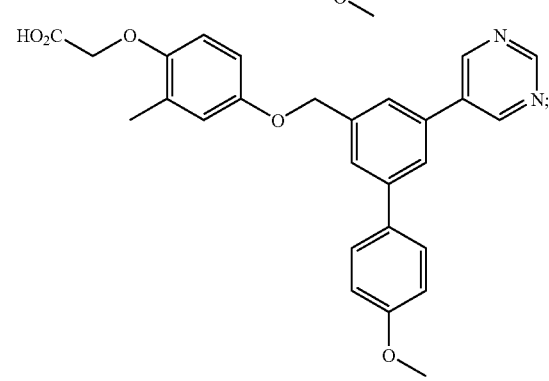
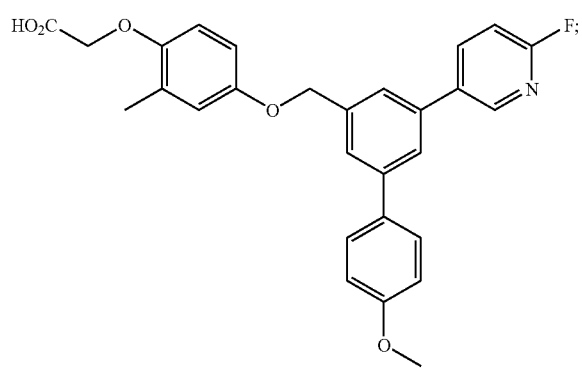
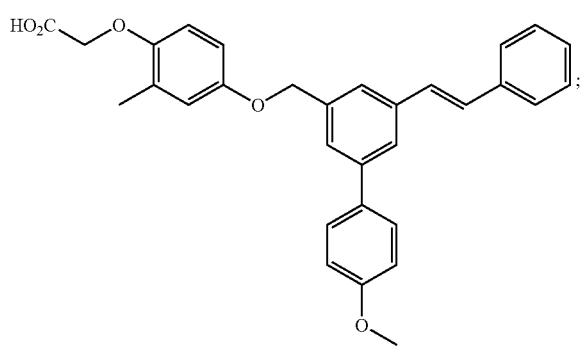
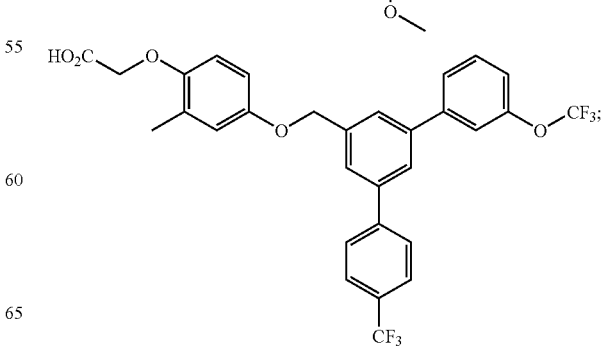

-continued
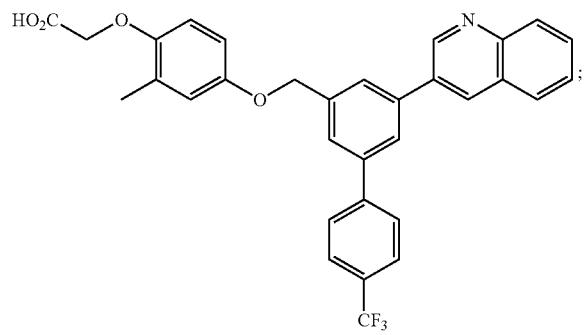
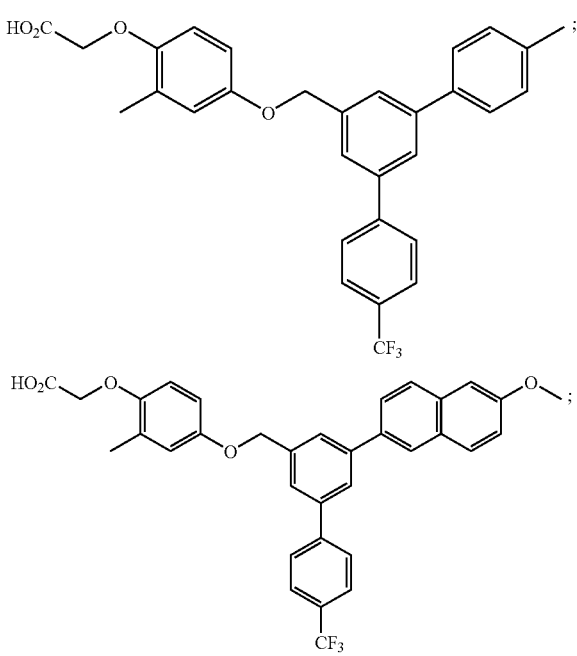

63
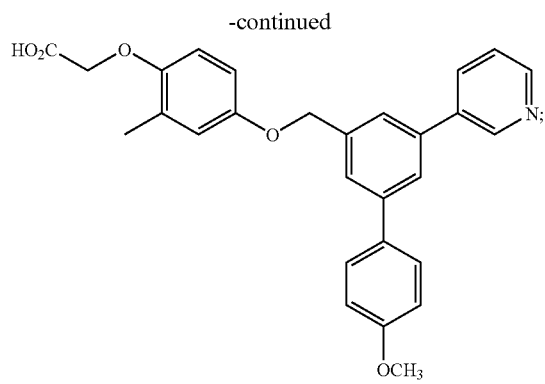
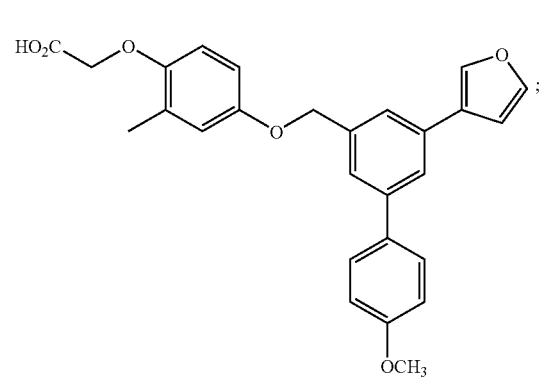
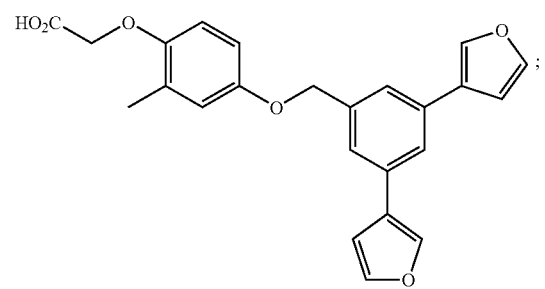
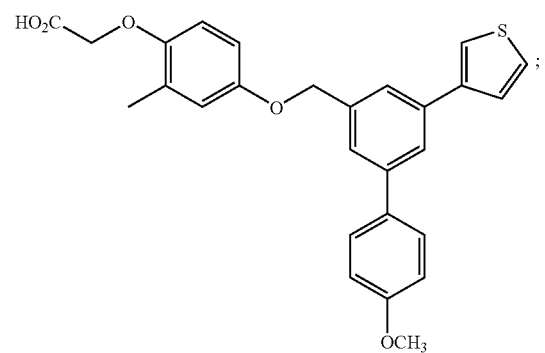
64
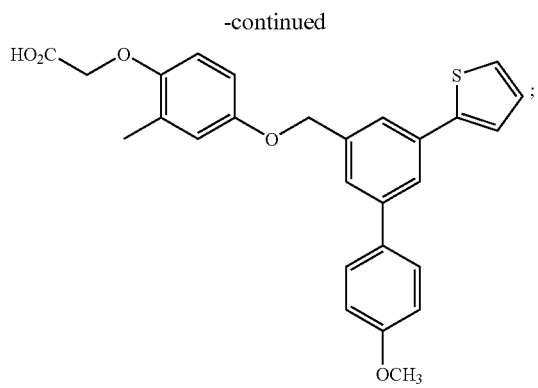
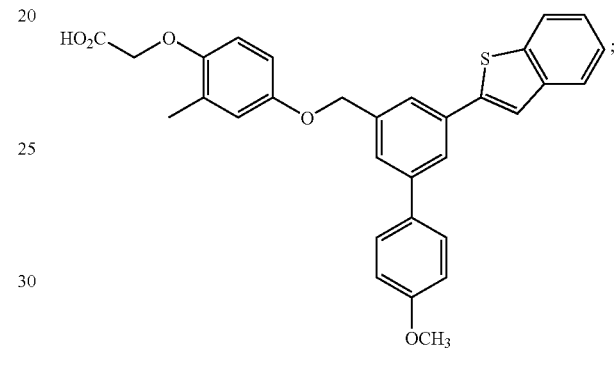
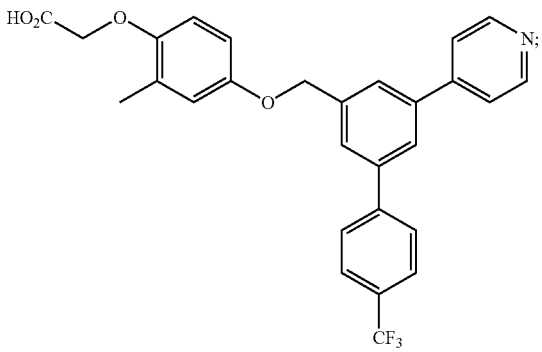
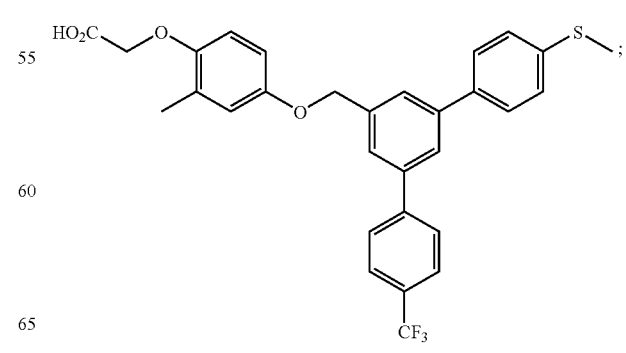

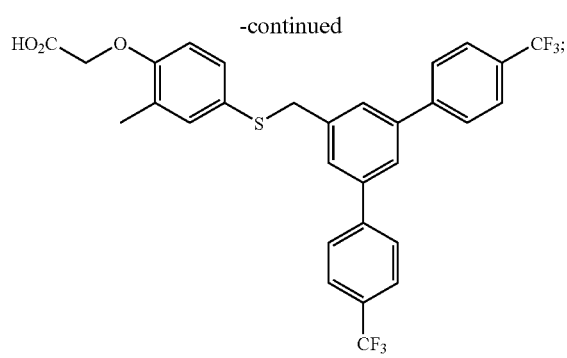
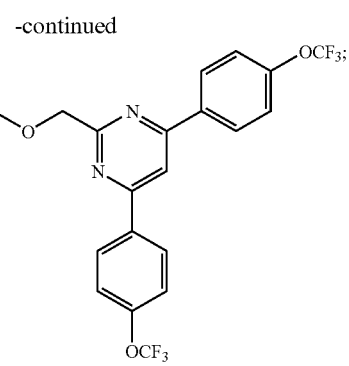
5. A pharmaceutical composition comprising a therapeutically effective amount of a compound of any of claim 1 in combination with one or more pharmaceutically acceptable excipients.
* * * * *